US008835138B2

(12) United States Patent
Solomon et al.

(10) Patent No.: US 8,835,138 B2
(45) Date of Patent: Sep. 16, 2014

(54) GLUCOSE VALVE AND OTHER METABOLITE VALVES

(75) Inventors: Kevin Solomon, Cambridge, MA (US); Tae Seok Moon, San Franciso, CA (US); Kristala Lanett Jones Prather, Milton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/638,026

(22) PCT Filed: Mar. 30, 2011

(86) PCT No.: PCT/US2011/030463
§ 371 (c)(1),
(2), (4) Date: Dec. 5, 2012

(87) PCT Pub. No.: WO2011/123504
PCT Pub. Date: Oct. 6, 2011

(65) Prior Publication Data
US 2013/0071894 A1 Mar. 21, 2013

Related U.S. Application Data

(60) Provisional application No. 61/318,965, filed on Mar. 30, 2010.

(51) Int. Cl.
| | | |
|---|---|---|
| *C12N 15/70* | (2006.01) | |
| *C12P 7/58* | (2006.01) | |
| *C12N 9/12* | (2006.01) | |
| *C07K 14/245* | (2006.01) | |
| *C12N 15/113* | (2010.01) | |
| *C12N 9/90* | (2006.01) | |

(52) U.S. Cl.
CPC . *C12N 15/70* (2013.01); *C12P 7/58* (2013.01); *C12N 9/1205* (2013.01); *C07K 14/245* (2013.01); *C12Y 207/01002* (2013.01); *C12N 2310/11* (2013.01); *C12N 15/1137* (2013.01); *C12Y 503/01009* (2013.01); *C12N 2310/111* (2013.01); *C12N 9/90* (2013.01)
USPC .......................... 435/137; 435/471; 435/252.3

(58) Field of Classification Search
CPC ................ C12P 7/06; C12P 7/18; C12P 7/42; C12P 19/24; C12P 7/02; C12P 7/10; C12P 7/14; C12P 7/20; C12P 7/6409; C12P 7/6463; C12P 7/649; C12P 9/00
USPC .............................................. 435/137, 252.33
See application file for complete search history.

(56) References Cited

U.S. PATENT DOCUMENTS

2003/0208057 A1 11/2003 Lewin et al.

OTHER PUBLICATIONS

Kawamoto et al., Implication of membrane localization of target mRNA in the action of a small RNA: mechanism of post-transcriptional regulation of glucose transporter in *Escherichia coli*. Genes Dev. 9: 328-338, 2005.*
Genbank Submission; NCBI, Accession No. M60615.1; Barnell et al.; BCT Apr. 26, 1993.
Genbank Submission; NCBI, Accession No. M12276.1; Lampel et al.; BCT Apr. 26, 1993.
Alper et al., Tuning genetic control through promoter engineering. Proc Natl Acad Sci U S A. Sep. 6, 2005;102(36):12678-83. Epub Aug. 25, 2005 Erratum in: Proc Natl Acad Sci U S A. Feb. 21, 2006;103(8):3006.
Bailey, Toward a science of metabolic engineering. Science. Jun. 21, 1991;252(5013):1668-75.
Baneyx, Recombinant protein expression in *Escherichia coli*. Curr Opin Biotechnol. Oct. 1999;10(5):411-21.
Bommarus et al., Novel biocatalysts: Recent developments. Chem Eng. Sci. Feb. 2006;61(3):1004-1016.
Chen et al., Comparative studies of *Escherichia coli* strains using different glucose uptake systems: Metabolism and energetics. Biotechnol Bioeng. Dec. 5, 1997;56(5):583-90.
Chotani et al., The commercial production of chemicals using pathway engineering. Biochim Biophys Acta. Dec. 29, 2000;1543(2):434-455.
Curtis et al., Phosphorylation of D-glucose in *Escherichia coli* mutants defective in glucosephosphotransferase, mannosephosphotransferase, and glucokinase. J Bacteriol. Jun. 1975;122(3): 1189-99.
Datsenko et al., One-step inactivation of chromosomal genes in *Escherichia coli* K-12 using PCR products. Proc Natl Acad Sci U S A. Jun. 6, 2000;97(12):6640-5.
De Anda et al., Replacement of the glucose phosphotransferase transport system by galactose permease reduces acetate accumulation and improves process performance of *Escherichia coli* for recombinant protein production without impairment of growth rate. Metab Eng. May 2006;8(3):281-90. Epub Mar. 6, 2006.
Desai et al., Antisense RNA strategies for metabolic engineering of *Clostridium acetobutylicum*. Appl Environ Microbiol. Mar. 1999;65(3):936-45.
Dong et al., Gratuitous overexpression of genes in *Escherichia coli* leads to growth inhibition and ribosome destruction. J Bacteriol. Mar. 1995;177(6):1497-504.
Ellison et al., Thermal regulation of beta-galactosidase synthesis using anti-sense RNA directed against the coding portion of the mRNA. J Biol Chem. Aug. 5, 1985;260(16):9085-7.
Engdahl et al., A two unit antisense RNA cassette test system for silencing of target genes. Nucleic Acids Res. Aug. 15, 1997;25(16):3218-27.
Farmer et al., Improving lycopene production in *Escherichia coli* by engineering metabolic control. Nat Biotechnol. May. 18, 2000;(5):533-7.
Flores et al., Pathway engineering for the production of aromatic compounds in *Escherichia coli*. Nat Biotechnol. May 1996;14(5):620-3.
Gadkar et al., Estimating optimal profiles of genetic alterations using constraint-based models. Biotechnol Bioeng. Jan. 20, 2005;89(2):243-51; published online Dec. 7, 2004.

(Continued)

*Primary Examiner* — Tekchand Saidha
*Assistant Examiner* — Rama P Ramanujam
(74) *Attorney, Agent, or Firm* — Wolf, Greenfield & Sacks, P.C.

(57) ABSTRACT

Aspects of the invention relate to the design and construction of Metabolite Valves, such as Glucose Valves, that can be used to divert metabolites from endogenous pathways toward alternative pathways in a cell.

8 Claims, 8 Drawing Sheets

(56) References Cited

OTHER PUBLICATIONS

Good, Translation repression by antisense sequences. Cell Mol Life Sci. May 2003;60(5):854-61.

Gosset, Improvement of *Escherichia coli* production strains by modification of the phosphoenolpyruvate:sugar phosphotransferase system. Microb Cell Fact. May 16, 2005;4(1):14.

Goward et al., The purification and characterization of glucokinase from the thermophile *Bacillus stearothermophilus*. Biochem J. Jul. 15, 1986;237(2):415-20.

Guzman et al., Tight regulation, modulation, and high-level expression by vectors containing the arabinose PBAD promoter. J Bacteriol. Jul. 1995;177(14):4121-30.

Hernández-Montalvo et al., Expression of galP and glk in a *Escherichia coli* PTS mutant restores glucose transport and increases glycolytic flux to fermentation products. Biotechnol Bioeng. Sep. 20, 2003;83(6):687-94.

Ji et al., Identification of critical staphylococcal genes using conditional phenotypes generated by antisense RNA. Science. Sep. 21, 2001;293(5538):2266-9.

Ji et al., Regulated antisense RNA eliminates alpha-toxin virulence in *Staphylococcus aureus* infection. J Bacteriol. Nov. 1999;181(21):6585-90.

Jiang et al., De novo computational design of retro-aldol enzymes. Science. Mar. 7, 2008;319(5868):1387-91. doi: 10.1126/science.1152692.

Karzai et al., the SsrA-SmpB system for protein tagging, directed degradation and ribosome rescue. Nat Struct Biol. Jun. 2000;7(6):449-55.

Keasling, Gene-expression tools for the metabolic engineering of bacteria. Trends Biotechnol. Nov. 1999;17(11):452-60.

Kernodle et al., Expression of an antisense hla fragment in *Staphylococcus aureus* reduces alpha-toxin production in vitro and attenuates lethal activity in a murine model. Infect Immun. Jan. 1997;65(1):179-84.

Kiely et al., Simple Preparation of Hydroxylated Nylons—Polyamides Derived from Aldaric Acids. ACS Symposium Series. May 5, 1994;575:149-158.

Kim et al., Down-regulation of acetate pathway through antisense strategy in *Escherichia coli*: improved foreign protein production. Biotechnol Bioeng. Sep. 30, 2003;83(7):841-53.

Lampel et al., Characterization of the developmentally regulated *Bacillus subtilis* glucose dehydrogenase gene. J Bacteriol. Apr. 1986;166(1):238-43.

Lee et al., Metabolic engineering towards biotechnological production of carotenoids in microorganisms. Appl Microbiol Biotechnol. Oct. 2002;60(1-2):1-11. Epub Aug. 24, 2002.

Leonard et al., Engineering microbes with synthetic biology frameworks. Trends Biotechnol. Dec. 2008;26 (12):674-81. doi: 10.1016/j.tibtech.2008.08.003. Epub Oct. 30, 2008.

Levine et al., Quantitative characteristics of gene regulation by small RNA. PLoS Biol. Sep. 2007;5(9):e229. Erratum in: PLoS Biol. Jan. 2008;6(1):e5.

Lippow et al., Progress in computational protein design. Curr Opin Biotechnol. Aug. 2007;18(4):305-11. Epub Jul. 20, 2007.

Makrides, Strategies for achieving high-level expression of genes in *Escherichia coli*. Microbiol Rev. Sep. 1996;60(3):512-38.

Mijts et al., Engineering of secondary metabolite pathways. Curr Opin Biotechnol. Dec. 2003;14(6):597-602.

Nakamura et al., Metabolic engineering for the microbial production of 1,3-propanediol. Curr Opin Biotechnol. Oct. 2003;14(5):454-9.

Nielsen, Metabolic engineering. Appl Microbiol Biotechnol. Apr. 2001;55(3):263-83.

Pestka et al., Anti-mRNA: specific inhibition of translation of single mRNA molecules. Proc Natl Acad Sci U S A. Dec. 1984;81(23):7525-8.

Pfeifer et al., Biosynthesis of complex polyketides in a metabolically engineered strain of *E. coli*. Science. Mar. 2, 2001;291(5509):1790-2.

Pfeifer et al., Biosynthesis of Yersiniabactin, a complex polyketide-nonribosomal peptide, using *Escherichia coli* as a heterologous host. Appl Environ Microbiol. Nov. 2003;69(11):6698-702.

Ro et al., Production of the antimalarial drug precursor artemisinic acid in engineered yeast. Nature. Apr. 13, 2006;440(7086):940-3.

Shimoni et al., Regulation of gene expression by small non-coding RNAs: a quantitative view. Mol Syst Biol. 2007;3:138. Epub Sep. 25, 2007.

Singh et al., Calcium glucarate prevents tumor formation in mouse skin. Biomed Environ Sci. Mar. 2003;16(1):9-16.

Singh et al., Induction of apoptosis by calcium D-glucarate in 7,12-dimethyl benz [a] anthracene-exposed mouse skin. J Environ Pathol Toxicol Oncol. 2007;26(1):63-73.

Snoep et al., Reconstruction of glucose uptake and phosphorylation in a glucose-negative mutant of *Escherichia coli* by using *Zymomonas mobilis* genes encoding the glucose facilitator protein and glucokinase. J Bacteriol. Apr. 1994;176(7):2133-5.

Tummala et al., Antisense RNA downregulation of coenzyme A transferase combined with alcohol-aldehyde dehydrogenase overexpression leads to predominantly alcohologenic *Clostridium acetobutylicum* fermentations. J Bacteriol. Jun. 2003;185(12):3644-53.

Tummala et al., Design of antisense RNA constructs for downregulation of the acetone formation pathway of *Clostridium acetobutylicum*. J Bacteriol. Mar. 2003;185(6):1923-34. Erratum in: J Bacteriol. May 2003;185(9):2973.

Van Den Berg et al., Reduction of the amount of periplasmic hydrogenase in *Desulfovibrio vulgaris* (Hildenborough) with antisense RNA: direct evidence for an important role of this hydrogenase in lactate metabolism. J Bacteriol. Jun. 1991;173(12):3688-94.

Wagner et al., Antisense RNA control in bacteria, phages, and plasmids. Annu Rev Microbiol. 1994;48:713-42.

Walaszek et al., d-Glucaric acid content of various fruits and vegetables and cholesterol-lowering effects of dietary d-glucarate in the rat. Nutrition Res. Apr. 1996;16(4):673-681.

Wang et al., Inducible antisense RNA expression in the characterization of gene functions in *Streptococcus mutans*. Infect Immun. Jun. 2005;73(6):3568-76.

Weisser et al., Functional expression of the glucose transporter of *Zymomonas mobilis* leads to restoration of glucose and fructose uptake in *Escherichia coli* mutants and provides evidence for its facilitator action. J Bacteriol. Jun. 1995;177(11):3351-4.

Werpy et al., Top Value added chemicals from biomass. vol. 1—results of screening for potential candidates from sugars and synthesis gas. PNNL and NREL. Aug. 2004.

Wilson et al., Antisense RNA to ahpC, an oxidative stress defence gene involved in isoniazid resistance, indicates that AhpC of *Mycobacterium bovis* has virulence properties. Microbiology. Oct. 1998;144 ( Pt 10):2687-95.

Yi et al., Altered glucose transport and shikimate pathway product yields in *E. coli*. Biotechnol Prog. Sep.-Oct. 2003;19(5):1450-9.

Genbank Submission; NCBI, Accession No. M60615.1; Barnell et al.; Apr. 26, 1993.

Hernández-Montalvo et al., Expression of galP and glk in a *Escherichia coli* PTS mutant restores glucose transport and increases glycolytic flux to fermentation products. Biotechnol Bioeng. Sep. 20,2003;83(6):687-94.

\* cited by examiner

SEQUENCE LISTING

```
<160> NUMBER OF SEQ ID NOS: 8

<210> SEQ ID NO 1
<211> LENGTH: 1422
<212> TYPE: DNA
<213> ORGANISM: Zymomonas mobilis

<400> SEQUENCE: 1
atgagttctg aaagtagtca gggtctagtc acgcgactag ccctaatcgc tgctataggc      60
ggcttgcttt tcggttacga ttcagcggtt atcgctgcaa tcggtacacc ggttgatatc     120
```

```
cattttattg cccctcgtca cctgtctgct acggctgcgg cttcccttttc tgggatggtc      180 gttgttgctg ttttggtcgg ttgtgttacc ggttcttttgc tgtctggctg gattggtatt     240
cgcttcggtc gtcgcggcgg attgttgatg agttccattt gtttcgtcgc cgccggtttt     300
ggtgctgcgt taaccgaaaa attatttgga accggtggtt cggctttaca aattttttgc     360 ttttccggt ttcttgccgg tttaggtatc ggtgtcgttt caaccttgac cccaacctat      420
attgctgaaa ttcgtccgcc agacaaacgt ggtcagatgg tttctggtca gcagatggcc     480
attgtgacgg gtgctttaac cggttatatc tttacctggt tactggctca tttcggttct    540
atcgattggg ttaatgccag tggttggtgc tggtctccgg cttcagaagg cctgatcggt     600
attgccttct tattgctgct gttaaccgca ccggatacgc cgcattggtt ggtgatgaag      660
ggacgtcatt ccgaggctag caaaatcctt gctcgtctgg aaccgcaagc cgatcctaat     720
ctgacgattc aaaagattaa agctggcttt gataaagcca tggacaaaag cagcgcaggt     780
ttgtttgctt ttggtatcac cgttgttttt gccggtgtat ccgttgctgc cttccagcag     840
ttagtcggta ttaacgccgt gctgtattat gcaccgcaga tgttccagaa tttaggtttt     900
ggagctgata cggcattatt gcagaccatc tctatcggtg ttgtgaactt catcttcacc    960
atgattgctt cccgtgttgt tgaccgcttc ggccgtaaac ctctgcttat ttggggtgct    1020
ctcggtatgg ctgcaatgat ggctgtttta ggctgctgtt tctggttcaa gtcggtggt    1080 gttttgcctt tggcttctgt gcttctttat attgcagtct ttggtatgtc atggggcct    1140 gtctgctggg ttgttctgtc agaaatgttc ccgagttcca tcaagggcgc agctatgcct    1200
atcgctgtta ccgacaatg gttagctaat atcttggtta acttcctgtt taaggttgcc    1260
gatggttctc cagcattgaa tcagactttc aaccacggtt tctcctatct cgttttcgca   1320
gcattaagta tcttaggtgg cttgattgtt gctcgcttcg tgccggaaac caaaggtcgg   1380
agcctggatg aaatcgagga gatgtggcgc tcccagaagt ag                       1422
```

<210> SEQ ID NO 2
<211> LENGTH: 35
<212> TYPE: DNA
<213> ORGANISM: Artificial
<220> FEATURE:
<223> OTHER INFORMATION: Primer For_gdh_subtilis

<400> SEQUENCE: 2
tacatataag tctagataac aaatggagga ggatg                                35

<210> SEQ ID NO 3
<211> LENGTH: 32
<212> TYPE: DNA
<213> ORGANISM: Artificial
<220> FEATURE:
<223> OTHER INFORMATION: Primer Rev_gdh_subtilis

<400> SEQUENCE: 3
caagtaacta aagctttcat gtctgggtcg ct                                   32

<210> SEQ ID NO 4
<211> LENGTH: 36
<212> TYPE: DNA
<213> ORGANISM: Artificial
<220> FEATURE:
<223> OTHER INFORMATION: Primer glk as rev -20

<400> SEQUENCE: 4
ctatgtcgac gatatcttta gcggagcagt tgaaga                               36

```
<210> SEQ ID NO 5
<211> LENGTH: 30
<212> TYPE: DNA
<213> ORGANISM: Artificial
<220> FEATURE:
<223> OTHER INFORMATION: Primer glk as for 100

<400> SEQUENCE: 5
ctatgaattc aataggtctt agcctgcgag                              30

<210> SEQ ID NO 6
<211> LENGTH: 30
<212> TYPE: DNA
<213> ORGANISM: Artificial
<220> FEATURE:
<223> OTHER INFORMATION: Primer glk as for 500

<400> SEQUENCE: 6
ctatgaattc ctattcggcg caaaatcaac                              30

<210> SEQ ID NO 7
<211> LENGTH: 29
<212> TYPE: DNA
<213> ORGANISM: Artificial
<220> FEATURE:
<223> OTHER INFORMATION: Primer glk as for 756

<400> SEQUENCE: 7
ctatgaattc gagattgagc gccagattg                               29

<210> SEQ ID NO 8
<211> LENGTH: 30
<212> TYPE: DNA
<213> ORGANISM: Artificial
<220> FEATURE:
<223> OTHER INFORMATION: Primer glk as for 953

<400> SEQUENCE: 8
ctatgaattc cctaaggtct ggcgtaaatg                              30
```

US 8,835,138 B2

GLUCOSE VALVE AND OTHER METABOLITE VALVES

RELATED APPLICATIONS

This application is a national stage filing under 35 U.S.C. §371 of international application PCT/US2011/030463, filed Mar. 30, 2011, which was published under PCT Article 21(2) in English, and claims the benefit under 35 U.S.C. §119(e) of U.S. Provisional Application Ser. No. 61/318,965, filed on Mar. 30, 2010, the disclosure of which is incorporated by reference herein in its entirety.

GOVERNMENT INTEREST

This invention was made with Government support under Grant No. EEC0540879 awarded by the National Science Foundation and Grant No. N000140510656 awarded by the Office of Naval Research. The government has certain rights in this invention.

FIELD OF THE INVENTION

The invention relates to metabolite valves that redirect metabolite flow from endogenous pathways toward heterologous ones.

BACKGROUND OF INVENTION

The discipline of metabolic engineering was defined fifteen years ago as "the improvement of cellular activities by manipulations of enzymatic, transport, and regulatory functions of the cell with the use of recombinant DNA technology" (Bailey 1991). Since that time, the field has witnessed a number of success stories with respect to the development of highly productive organisms, especially microbes. Initially, metabolic engineering efforts were primarily focused on improving the productivity of naturally-occurring metabolites in the target organisms, as is consistent with Bailey's original definition. More recently, the field has expanded to encompass a number of examples of introducing new enzyme activities into a host cell in order to produce non-natural products (Nielsen 2001). Non-natural products are defined in this case as compounds that are foreign to the production organism. Thus, such compounds may still be found in other organisms (e.g., plant natural products), or they may be novel, structurally distinct from those known to exist in nature.

Significant efforts have gone into the development of microorganisms to produce non-natural products. Examples include polyketides, with anti-infective, anti-tumor, and cholesterol-lowering properties (Pfeifer et al. 2001; Pfeifer et al. 2003); and isoprenoids, a class of compounds with uses that range from pigments (Mijts and Schmidt-Dannert 2003) to the treatment of malaria (Ro et al. 2006). The development of a fermentation process for the production of 1,3-propanediol at titers that exceed 125 g/L illustrates that the use of microbial chemical factories extends well beyond the synthesis of human therapeutics (Nakamura and Whited 2003). The advent of tools such as directed evolution and advances in the ability to rationally engineer or re-engineer proteins with desired activities against specified substrates enables one to imagine the ability to produce proteins capable of transforming an enormous range of chemical compounds into novel products (Lippow and Tidor 2007; Jiang et al. 2008). Indeed, efforts in biocatalysis have resulted in the identification of many enzymes displaying novel activities, which themselves are ideal candidates for directed evolution to expand the substrate and product repertoire even further (Bommarius and Polizzi 2006). Assembling several such proteins—either native or evolved towards optimal activity against a particular substrate—into a functioning metabolic pathway can result in the microbial production of a non-natural product. It is now conceivable that the production of many compounds of commercial value, traditionally reserved for the synthetic organic chemist, can be achieved with microbial systems.

One of the limitations for productivity that often arise in the development of microbial chemical factories is low product yield. Typical approaches towards increasing yields in metabolic engineering involve deleting the genes that encode for competing activities; however, this is not feasible when the mutation might severely limit cell growth or be lethal.

SUMMARY OF INVENTION

Described herein is a new paradigm for metabolic engineering in which "Metabolite Valves" are employed to re-direct metabolite flow from endogenous pathways towards heterologous ones in a temporal, controlled fashion. In this way, secondary metabolism can be artificially engineered such that growth is allowed to proceed at an optimal rate to accumulate biomass and the necessary enzymes to mediate the desired conversions, then product formation is favored at the expense of additional growth. Herein, the principles of Metabolite Valve design and constructions are demonstrated through the development of a set of Glucose Valves for the production of glucose-derived metabolites, including gluconate and glucaric acid in cells.

Aspects of the invention relate to methods for redirecting glycolytic flux in a cell, including reducing expression of the phosphoenolpyruvate (PEP)-dependent glucose phosphotransferase system (PTS) in the cell and inhibiting phosphorylation of glucose by glucokinase within the cell. In some embodiments, the cell has increased expression of galactose permease (galP) and/or glucose facilitator protein (glf).

Aspects of the invention relate to inhibiting phosphorylation of glucose by glucokinase within the cell by reducing expression of glucokinase in the cell. In some embodiments, reducing expression of glucokinase in the cell involves recombinantly expressing in the cell an antisense RNA transcript that targets glucokinase. In certain embodiments, the antisense RNA transcript comprises at least 10%, at least 50%, at least 75% or at least 95% of the open reading frame of glucokinase. In some embodiments, the antisense RNA transcript includes the ribosome binding site (RBS).

In some embodiments, the antisense RNA transcript is expressed from an inducible plasmid vector. In certain embodiments, the antisense RNA transcript is expressed under the control of the $P_{tet}$ promoter. In some embodiments, methods further involve contacting the cell with an inducer, such as anhydrotetracycline (aTc). In some embodiments, expression of glucose-6-phosphate isomerase in the cell is reduced, such as by expressing in the cell an antisense RNA transcript that targets glucose-6-phosphate isomerase.

In some embodiments, the promoter of glucokinase is replaced by a repressible promoter. The cell can recombinantly express an inducible repressor protein that represses glucokinase expression. In some embodiments, the cell is a microbial cell. In certain embodiments, the microbial cell is a bacterial cell such as an *Escherichia coli* cell. In some embodiments, the cell is a eukaryotic cell such as a fungal cell, a yeast cell, an insect cell, a plant cell or a mammalian cell.

Aspects of the invention involve methods of producing gluconate and/or glucaric acid including culturing a cell associated with the invention and optionally recovering gluconate and/or glucaric acid from the cell. In some embodiments, the cell recombinantly expresses a gene encoding for glucose dehydrogenase (gdh). In certain embodiments, the gene encoding for glucose dehydrogenase is a *Bacillus* gene such as a *Bacillus subtilis* gene.

In some embodiments, reducing expression of the phosphoenolpyruvate (PEP)-dependent glucose phosphotransferase system (PTS) involves reducing or eliminating expression of the operon ptsHI-crr. In some embodiments, the cell recombinantly expresses a gene encoding for galactose permease (galP) and/or glucose facilitator protein (glf). In certain embodiments, the cell recombinantly expresses a *Zymomonas* gene, such as a *Zymomonas mobilis* gene, encoding for glucose facilitator protein (glf).

Aspects of the invention relate to recombinant cells that have reduced expression of the phosphoenolpyruvate (PEP)-dependent glucose phosphotransferase system (PTS) and which overexpress one or more of galactose permease (galP) and glucose facilitator protein (glf). In some embodiments, expression of glucokinase in the cell is reduced. In some embodiments, the cell recombinantly expresses an antisense RNA transcript that targets glucokinase. In certain embodiments, the antisense RNA transcript comprises at least 10%, at least 50%, at least 75%, or at least 95% of the open reading frame of glucokinase. In some embodiments, the antisense RNA transcript includes the ribosome binding site (RBS).

In some embodiments, the antisense RNA transcript is expressed from an inducible plasmid vector. In certain embodiments, the antisense RNA transcript is expressed under the control of the $P_{tet}$ promoter. In some embodiments, expression of glucose-6-phosphate isomerase in the cell is reduced, such as by expressing in the cell an antisense RNA transcript that targets glucose-6-phosphate isomerase.

In some embodiments, the promoter of glucokinase is replaced by a repressible promoter. The cell can recombinantly express an inducible repressor protein that represses glucokinase expression. In some embodiments, the cell is a microbial cell. In certain embodiments, the microbial cell is a bacterial cell such as an *Escherichia coli* cell. In some embodiments, the cell is a eukaryotic cell such as a fungal cell, a yeast cell, an insect cell, a plant cell or a mammalian cell.

In some embodiments, reduced expression of the phosphoenolpyruvate (PEP)-dependent glucose phosphotransferase system (PTS) involves reduced or eliminated expression of the operon ptsHI-crr. In some embodiments, the cell recombinantly expresses a gene encoding for galactose permease (galP) and/or glucose facilitator protein (glf). In certain embodiments, the cell recombinantly expresses a *Zymomonas* gene, such as a *Zymomonas mobilis* gene, encoding for glucose facilitator protein (glf). In some embodiments, the cell recombinantly expresses a gene encoding for glucose dehydrogenase (gdh). In certain embodiments, the gene encoding for glucose dehydrogenase is a *Bacillus* gene such as a *Bacillus subtilis* gene.

Aspects of the invention relate to methods for producing a metabolite of glucose, including culturing a cell associated with the invention and optionally recovering the metabolite of glucose from the cell and/or cell culture. In some embodiments, the metabolite of glucose is gluconate and/or glucaric acid. Further aspects of the invention relate to cell cultures produced by cells associated with the invention wherein the cell culture comprises gluconate and/or glucaric acid.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
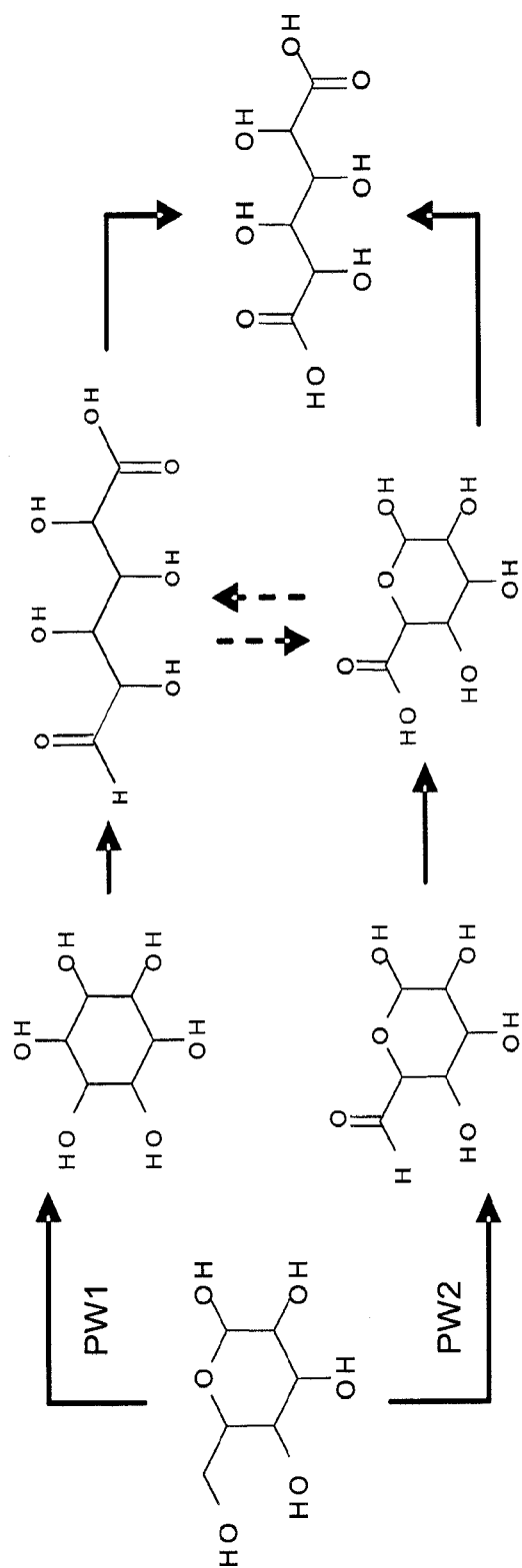
FIG. 1 presents a schematic of proposed biosynthetic routes from glucose to glucaric acid. Chirality of structures is omitted from the schematic for visual clarity. The first arrow of PW1 represents 3 chemical transformations, but only one cloned enzyme in *E. coli* (Hansen et al, 1999), in which the substrate is glucose-6-phosphate. The first conversion step of PW2 utilizes un-phosphorylated glucose as a substrate.

Metabolic engineering has produced many examples of successful and optimized production of biochemicals, including the production of biochemicals in an organism in which the compound does not naturally occur. However, a common problem faced by such systems is low product yield (meaning the fraction of the carbon substrate converted to product) that results from the need to consume substrate in order to produce high biocatalytic capacity in the form of biomass. Described herein is the development of tools that address this limitation. The invention is based, at least in part, on the surprising discovery that Metabolite Valves can be designed and constructed as a mechanism for diverting a substrate from biomass synthesis towards product formation in a controlled manner. A Glucose Valve is demonstrated that is able to redirect glycolytic flux in a cell, with applications for the synthesis of any product that can be derived directly from glucose. Metabolite Valves offer a novel approach to facilitating the metabolic engineering of biosynthetic pathways for the production of a variety of organic compounds in microbial chemical factories.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Glucose is commonly used as a carbon and energy source for metabolic engineering. Glucose Valves described herein have the potential to significantly increase the efficiency of product formation in metabolic engineering by diverting glucose from glycolysis and the pentose phosphate pathway to alternative pathways, such as heterologous pathways, in a cell. Glucose Valves alter glycolytic flux by altering glucose transport and inhibiting glucose phosphorylation.

Aspects of the invention relate to altering glucose transport. In some aspects, glucose transport is altered by reducing or eliminating expression of the phosphoenolpyruvate (PEP)-dependent glucose phosphotransferase system (PTS). Glucose that enters a cell through the PTS system is phosphorylated with the consumption of PEP, whereas when PTS is knocked out, glucose enters the cell in an unphosphoryated state. In some embodiments, reducing or eliminating expression of PTS involves reducing or eliminating expression of one or more components of the PTS that are required for phosphorylation of glucose even when lower affinity transporters are intact. For example, one or more of the genes within the ptsHI-crr operon can be targeted to reduce or eliminate expression of PTS. ptsH and ptsI encode the phosphohistidine carrier protein (HPr) and Enzyme I (EI) respectively. crr encodes Enzyme $IIA^{Glc}$. Reduction or elimination of expression of one or more components of the ptsHI-crr operon can be achieved using techniques known to those of ordinary skill in the art. For example, the ptsHI-crr operon can be knocked out using the method of Datsenko and Wanner, 2000. In some embodiments, expression of one or more components of the manXYZ operon, encoding the $IIAB^{man}$ homodimer enzyme and the integral membrane permease $IICD^{man}$, is also reduced or eliminated.

PTS mutants, such as mutants in which the ptsHI-crr operon is knocked out, exhibit altered growth and metabolic profiles and can result in cells that exhibit slow growth with glucose as a sole carbon source. One of the options for restoring robust glucose utilization is to increase expression of the galactose permease gene (galP). In some embodiments, increasing expression of galP involves altering or replacing the promoter of the endogenous gene, including for example, replacing the endogenous promoter of galP with a constitutive promoter.

As one of ordinary skill in the art would appreciate, any appropriate constitutive promoter can be used, for example, in some embodiments, the $lacI^q$ promoter (MIT Registry of Standard Parts, parts.mit.edu, Part I14032) is used. In some embodiments a galP gene, such as a constitutively expressed galP gene, is expressed recombinantly, with or without the simultaneous presence of an endogenous gene. In some embodiments, multiple copies of a recombinant and/or endogenous galP gene are expressed in the same cell. In certain embodiments, glucokinase (glk) expression is also increased in the cell. In previous reports, combined up-regulation of a permease and overexpression of glk restored cell growth rates in PTS-deficient mutants to nearly 90% of PTS-active strains (Hernandez-Montalvo et al. 2003; Gosset, 2005). However, in some embodiments, constitutive expression of galP is sufficient to restore growth rates of PTS-deficient strains to growth rates approximating PTS active cells without overexpression of glk. For example, the E. coli KTS-022 strain described in the Examples section, in which the ptsHI-crr operon is knocked out and the galP gene is constitutively expressed, exhibits the same growth rate and achieves the same cell densities as the E. coli DH10B parent strain.

A second and non-exclusive option for restoring robust glucose utilization in PTS deficient cells is to express a glucose facilitator protein (glf). In some embodiments, a glf gene is endogenously expressed in a cell and the expression of the endogenous gene is upregulated such as through modifying or replacing its promoter. In some embodiments, glf is expressed recombinantly in a cell, whether or not there is an endogenous copy of the gene. It should be appreciated that any glf gene from any organism can be compatible with aspects of the invention. One of ordinary skill in the art would understand how to determine, using methods described in the specification, and/or methods known in the art, whether a glf gene from a given organism can partially or fully restore glucose utilization in PTS deficient cells by comparing PTS deficient cells that express the glf gene from a given organism with PTS deficient cells that do not express the glf gene from the given organism. The glf gene can be a bacterial gene such as a *Zymomonas* gene. In some embodiments, the *Zymomonas* glf gene is a *Zymomonas mobilis* gene represented by GenBank Accession number M60615/M37982.

A second aspect of the Glucose Valve involves inhibiting phosphorylation of glucose by glucokinase (Glk) in the cell Inhibiting phosphorylation of glucose by Glk can be achieved by reducing expression and/or activity of Glk in the cell. As one of ordinary skill in the art would appreciate, reduction of Glk expression and/or activity can be achieved by targeting glk DNA, mRNA or protein. For example, transcription, mRNA degradation, translation, post-translational modification and protein degradation all represent stages of Glk expression and/or activity that can be targeted. In some embodiments, more than one of these stages of Glk expression and/or activity is targeted in order to inhibit phosphorylation of glucose by Glk.

In some embodiments, glk transcription is manipulated, such as through the use of a titratable promoter. For example, the native promoter of glk can be replaced with a repressible promoter and placed under the control of a repressor protein. Several non-limiting examples of repressible promoters and corresponding repressor proteins include Tet/TetR, Lac/LacI and lambda promoter/cI. One of ordinary skill in the art would appreciate that many repressible promoters and corresponding repressor proteins would be compatible with aspects of the invention. The repressor protein can be placed under the control of an inducer through the use of an inducible promoter. In such a system, the default state is constitutive expression of glk, while the addition of an inducer results in down-regulation of glk expression. Such a system can be referred to as a "genetic inverter" meaning that output (glk expression) is high when the input concentration (inducer) is low, and the output is low when the input concentration is high (Registry of Standard Biological Parts, partsregistry.org).

In some embodiments, the glk promoter is replaced with a promoter based on the lambda promoter (Alper et al. 2005) or a promoter derived from the sigma-70 consensus sequence from *E. coli* promoters (partsregistry.org). It should be appreciated that a variety of promoters with varying strengths can be compatible with aspects of the invention and the effectiveness of such promoters can be tested by one of ordinary skill in the art using routine experimentation.

In one embodiment, a genetic inverter is used, as described in the Registry of Standard Biological Parts (partsregistry.org, Part BBa_J5516). In this design, the glk promoter is replaced with the lambda promoter. Adjacent to the lambda promoter is a LacI operator site, enabling repression by LacI. The lacI gene can be incorporated upstream under the control of an inducible promoter such as the $P_{BAD}$ promoter. In this example, addition of arabinose in the presence of the AraC activator/repressor protein results in expression of the LacI repressor protein and down-regulation of glk expression. In some embodiments, the lacI repressor gene is placed under the control of the anhydrotetracycline (aTc)-inducible $P_{tet}$ promoter, repressed by the TetR repressor. In this example, in the absence of aTc, LacI repressor concentration is low and glk expression is high. Upon addition of aTc, LacI repressor concentration increases causing a correlative decrease in glk expression and Glk activity. It should be appreciated that this embodiment represents a non-limiting example and embodiments that utilize other promoters, repressors and inducers are also compatible with Glucose Valve designs.

A second and nonexclusive approach to reducing expression and/or activity of Glk is to target translation of glk mRNA through the use of antisense RNA (asRNA) targeted to glk. asRNA, which was first observed in microbial systems, typically functions by inhibiting translation of a sense messenger RNA template (Wagner and Simons 1994; Good 2003). The use of asRNA in engineered microbial systems is particularly useful for reducing gene expression in instances where a knock-out may be lethal. In some instances of metabolic engineering, asRNA has been reported to reduce enzyme activity by as much as 86% and improve production of a desired product by as much as 3-fold (Desai and Papoutsakis 1999; Tummala et al. 2003a; Tummala et al. 2003b).

asRNAs of varying lengths that target glk are compatible with aspects of the invention. Natural microbial asRNAs vary in length from approximately 50-200 nucleotides (Good 2003) while engineered transcripts have typically ranged from approximately 150 to over 2500 nucleotides (Kim and Cha 2003; Ellison et al. 1985). The glk open reading frame is 966 nucleotides. In some embodiments, the asRNA transcript comprises at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, of the length of the glk open reading frame, including all intermediate values. In some embodiments, the ribosome binding site is included in the asRNA transcript, while in other embodiments, it is not. In some embodiments, the asRNA is a direct inversion of the glk open reading frame and 5'UTR. In certain embodiments, the asRNA comprises approximately 95% of the glk open reading frame and includes the ribosome binding site.

It should be appreciated that the percent down-regulation of Glk expression and/or activity will depend, at least in part, on the asRNA transcript. In some instances the asRNA transcript will result in approximately a 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or more than 99% reduction in Glk expression and/or activity.

The asRNA can be expressed recombinantly under the control of an inducible promoter. In some embodiments, the promoter is the $P_{tet}$ promoter, inducible with the addition of anhydrotetracycline (aTc). As demonstrated in the Examples section, asRNA transcripts targeting glk and expressed under the control of the $P_{tet}$ promoter were effective in achieving Glk downregulation relative to a control and redirecting glycolytic flux. It should be appreciated that other promoters and inducers are also compatible with aspects of the invention as would be understood by one of ordinary skill in the art.

The asRNA can be expressed from a low, medium or high-copy plasmid. In some embodiments, it is expressed from a multi-copy plasmid to produce sufficient copies of the asRNA to promote hybridization. In some embodiments, a moderately low-copy plasmid, for example with a p15A replicon, is used to minimize the effects of background expression of the asRNA.

As would be understood by one of ordinary skill in the art, the effective concentration of the inducer, such as aTc, can vary depending on the application for which the Glucose Valve is used. Optimal concentration of the inducer, for a given application, can be determined without undue experimentation. For example, in some embodiments, the inducer is added at approximately 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or more than 990 ng/ml including all intermediate values.

The timing of induction is also a parameter that can be optimized as would be understood by one of ordinary skill in the art. In some embodiments, a single inducer concentration is added to the cell culture at a single time point. In other embodiments, the inducer can be added multiple times, either at the same concentration each time or at different concentrations.

One advantage of the valve design is the ability to modulate the degree to which the valve is open, for example through structural differences in the asRNA transcripts that impact the hybridization effectiveness, or through titration of the levels of asRNA, or through addition of greater or lesser amounts of an inducer such as aTc or arabinose to regulate amounts of repressor protein produced to regulated gene transcription.

In some embodiments, expression of glucose-6-phosphate isomerase in the cell is also reduced, such as through recombinantly expressing an asRNA targeting the gene encoding for this enzyme.

As one of ordinary skill in the art would be aware, genes that are homologous to the genes recombinantly expressed according to aspects of the invention could be obtained from other species and could be identified by homology searches, for example through a protein BLAST search, available at the National Center for Biotechnology Information (NCBI) internet site (ncbi.nlm.nih.gov). Genes associated with the invention can be amplified from DNA from any source of DNA which contains the given gene, such as using polymerase chain reaction (PCR) amplification. In some embodiments, genes associated with the invention are synthetic. Any means of obtaining a gene encoding enzymes associated with the invention are compatible with the instant invention.

The invention involves recombinant expression of genes encoding enzymes discussed above, functional modifications and variants of the foregoing, as well as uses relating thereto. Homologs and alleles of the nucleic acids associated with the invention can be identified by conventional techniques. The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 90% amino acid identity to the sequences of nucleic acids and polypeptides, respectively, in some instances will share at least 90%, 91%, 92%, 93%, 94%, 95%, 96%, 97%, 98% or 99% nucleotide identity and/or at least 95%, 96%, 97%, 98% or 99% amino acid identity. The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/ 0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C. There are other conditions, reagents, and so forth which can be used, which result in a similar degree of stringency. The skilled artisan will be familiar with such conditions, and thus they are not given here.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide, for example, 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence.

One of ordinary skill in the art will be familiar with methods for predicting the effect on protein conformation of a change in protein sequence, and can thus "design" a variant of a polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or eukaryotic expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

The invention encompasses any type of cell including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp.,

*Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In some embodiments, the cell is an *E. coli* DH10B cell.

In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. In some embodiments, the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments the cell is an algal cell, a plant cell, or a mammalian cell. It should be appreciated that some cells compatible with the invention may express an endogenous copy of one or more of the genes associated with the invention as well as a recombinant copy. In some embodiments if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein, including pathways for the production of gluconate and/or glucaric acid. It should be appreciated that the principles of altering glucose transport and phosphorylation in order to alter glycolytic flux are compatible with multiple cell types. The specific aspects of the Glucose Valve design can be optimized as appropriate for different cell types. For example, one or more elements of a Glucose Valve can be changed to make individual test cells or strains, and such cells or strains tested for one or more properties, such as production of a desired product, e.g., one or more metabolites. An example of this is shown herein, wherein the elements of a Glucose Valve (e.g., antisense constructs, regulatory elements, promoters) were tested in combination, followed by measurement of molar gluconate production.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes associated with the invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989 or *Current Protocols in Molecular Biology*, F. M. Ausubel, et al., eds., John Wiley &

Sons, Inc., New York. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for example for production of gluconate, is demonstrated in the Examples section using *E. coli*. Glucose Valves are also compatible with other bacterial cells and the concept can also be extended to non-bacterial cells.

A nucleic acid molecule that encodes an enzyme associated with the invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments, one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, amino acids, antibiotics, IPTG for gene induction, ATCC Trace Mineral Supplement, and inducers such as aTc, according to aspects of the invention. Similarly, other aspects of the medium, and growth conditions of the cells of the invention can be optimized through routine experimentation. For example, pH, temperature, and concentration and timing of induction of glk repression are non-limiting examples of factors which can be optimized.

In some embodiments, factors such as choice of media, media supplements, and temperature can influence production levels of glucose metabolites such as gluconate and/or glucaric acid. In some embodiments the concentration and amount of a supplemental component such as an inducer can be optimized. For example, how often the media is supplemented with one or more supplemental components such as one or more inducers, and the amount of time that the media is cultured before harvesting the glucose metabolite can be optimized.

Aspects of the invention relate to using Glucose Valves to divert glucose from endogenous to heterologous pathways in a cell. As would be understood by one or ordinary skill in the art, Glucose Valves could be used to produce or increase production of any metabolite of glucose. In some embodiments, the metabolite is gluconate and/or glucaric acid. As presented in the Examples section, in some embodiments, use of a Glucose Valve produced at least 3-fold more gluconate in an induced sample than in an uninduced sample. In some embodiments, gluconate specific productivity increased 8-fold relative to an aTc-induced empty vector control and 3-fold relative to a control consisting of an uninduced vector containing the asRNA. In certain embodiments, the level of gluconate production corresponded to a molar yield of gluconate on glucose that was 2.5-fold higher for an induced culture than an uninduced culture, and 5-fold higher than a control.

In some embodiments, the molar yield of a glucose metabolite, such as gluconate or glucaric acid, using a Glucose Valve is at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9 or 15.0 fold higher than that of a control, including all intermediate values. The titer produced for a given product will be influenced by multiple factors including choice of media, choice of promoters and inducers, and level of induction.

In some embodiments, wherein the Glucose Valve is used for production of gluconate, the cell can recombinantly express a gene encoding for glucose dehydrogenase (gdh). The gdh gene can be a bacterial gene such as a *Bacillus* gene. In certain embodiments, the gdh gene is a *Bacillus subtilis* gene.

The liquid cultures used to grow cells associated with the invention can be housed in any of the culture vessels known and used in the art. In some embodiments large scale production in an aerated reaction vessel such as a stirred tank reactor can be used to produce large quantities of a glucose metabolite such as gluconate and/or glucaric acid.

Aspects of the invention include strategies to optimize production of glucose metabolites such as gluconate and/or glucaric acid from a cell. Optimized production of a glucose metabolite refers to producing a higher amount of a glucose metabolite following pursuit of an optimization strategy than would be achieved in the absence of such a strategy. One strategy for optimization is to increase expression levels of one or more genes associated with the invention through selection of appropriate promoters and ribosome binding sites. In some embodiments this may include the selection of high-copy number plasmids, or low or medium-copy number plasmids. The step of transcription termination can in some instances also be targeted for regulation of gene expression, through the introduction or elimination of structures such as stem-loops.

In some embodiments it may be advantageous to use a cell that has been optimized for production of glucose metabolites such as gluconate and/or glucaric acid. In some embodiments, screening for mutations that lead to enhanced production of glucose metabolites such as gluconate and/or glucaric acid may be conducted through a random mutagenesis screen, or through screening of known mutations. In some embodiments shotgun cloning of genomic fragments could be used to identify genomic regions that lead to an increase in production of glucose metabolites such as gluconate and/or glucaric acid, through screening cells or organisms that have these fragments for increased production of glucose metabolites such as gluconate and/or glucaric acid. In some cases one or more mutations may be combined in the same cell or organism.

Optimization of production of glucose metabolites such as gluconate and/or glucaric acid can involve optimizing selection of bacterial strains for expression of recombinant pathways described herein. In some embodiments, use of a bacterial strain that is close to wild-type, meaning a strain that has not been substantially genetically modified, may lead to increased titers of glucose metabolites such as gluconate and/or glucaric acid.

Optimization of protein expression may also require in some embodiments that a gene encoding an enzyme be modified before being introduced into a cell such as through codon optimization for expression in a bacterial cell. Codon usages for a variety of organisms can be accessed in the Codon Usage Database (kazusa.or.jp/codon/).

In some embodiments, protein engineering can be used to optimize expression or activity of one or more enzymes associated with the invention. In certain embodiments a protein engineering approach could include determining the three dimensional (3D) structure of an enzyme or constructing a 3D homology model for the enzyme based on the structure of a related protein. Based on 3D models, mutations in an enzyme can be constructed and incorporated into a cell or organism, which could then be screened for an increased production of glucose metabolites such as gluconate and/or glucaric acid. In some embodiments production of glucose metabolites such as gluconate and/or glucaric acid in a cell could be increased through manipulation of enzymes that act in the same pathway as the enzymes associated with the invention. For example in some embodiments it may be advantageous to increase expression of an enzyme or other factor that acts upstream of a target enzyme such as an enzyme associated with the invention. This could be achieved by over-expressing the upstream factor using any standard method.

Methods and compositions described herein for Glucose Valves have widespread applications. For pathways where glucose is directly utilized as a substrate for production, Glucose Valves have the potential to increase productivity by redirecting glucose away from glycolysis. An example of such a pathway is the production of glucaric acid, a compound that is difficult to make through traditional synthesis and which has a market estimated between $7-20 billion USD annually. Glucose Valves would also be valuable in existing pathways, such as carotenoid production, where glycolysis intermediates are required for production, and which has an estimated market of $1 billion USD annually. For example, by controlling glycolytic flux, incorporation of glucose into lycopene can be maximized by reducing the amount of excess carbon flowing through glycolysis which is ultimately wasted as acetate and other anaerobic products. The potential for dynamic control, using the Glucose Valves is also favorable for optimizing pathway productivity. This system can be implemented to de-couple growth and product formation for any pathway originating from glucose, for example, for the production of furans, identified as top value-added products in Werpy and Paterson 2004, and for the production of polysaccharides.

The valve concept can be extended to other metabolites and other organisms. As discussed in the Examples section, mathematical description of a Valve such as the Glucose Valve, allows for the establishment of a design methodology that facilitates design and construction of similar devices for any metabolite. For example, mathematical modeling allows for a quantitative determination of the effect of varying parameters such as protein half-life, and identifies parameters that are amenable to alteration for optimizing Valve operation. For example, degradation tags such as ssrA tags can be added to a peptide sequence to promote degradation and reduce half-life of the target protein (Karzai et al. 2000).

EXAMPLES

Example 1

Establishment of Concepts Underlying Glucose Valve Construction

Figure 2:
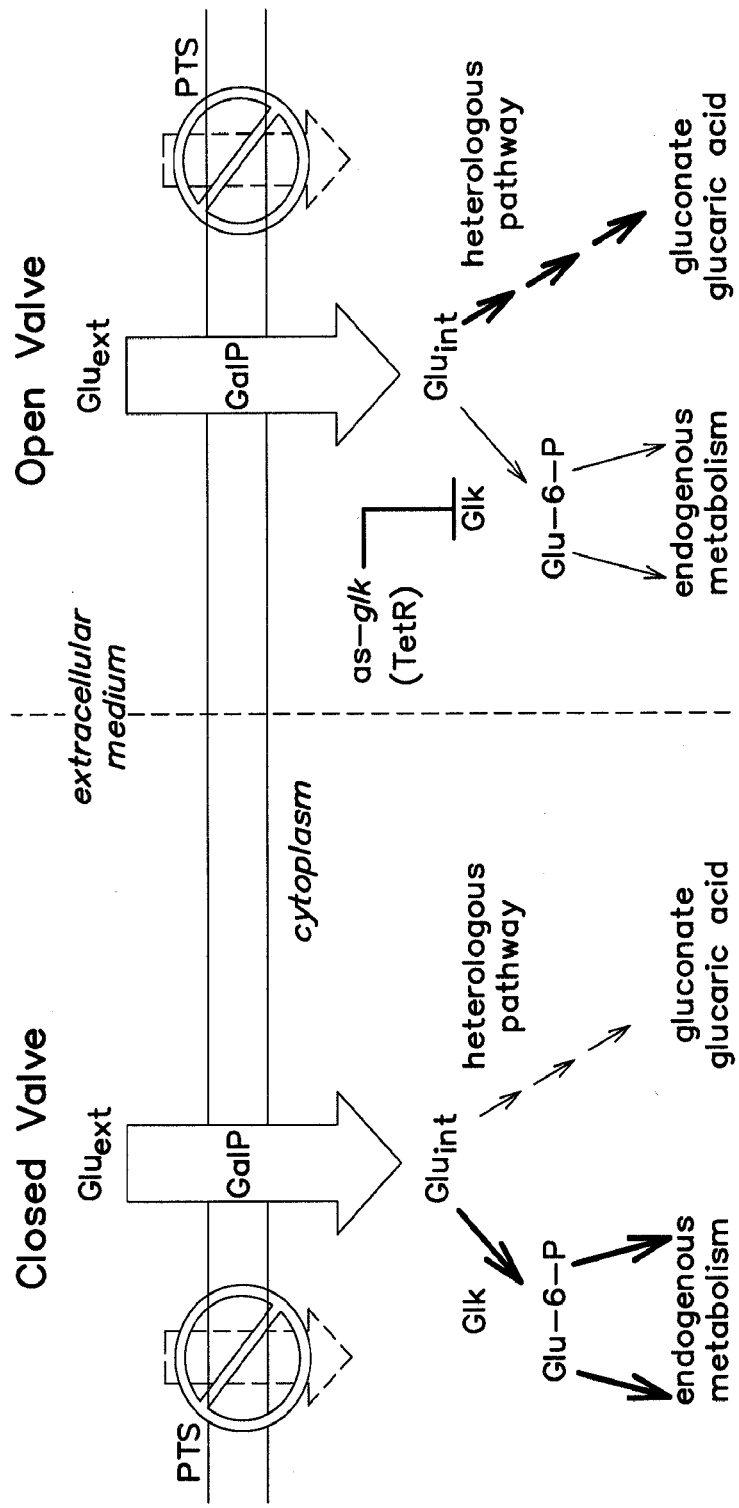
FIG. 2 presents a schematic of the design and implementation of the Glucose Valve. Glucose transport is altered through mutations in the PTS system. Glucokinase expression can be regulated by, for example, an antisense RNA transcript, or by direct regulation by a repressor protein if the natural promoter/operator of the glk gene is replaced. The tet repressor is shown as a representative repressor protein. PTS=PEP-dependent phosphotransferase, GalP=galactose permease, Glk=glucokinase, Glu=glucose (ext=extracellular, int=intracellular), Glu-6-P=glucose-6-phosphate, as-glk=Glk antisense RNA, TetR=tet repressor.

Described herein is a novel approach to producing glucaric acid from glucose in *E. coli*. Glucose as a starting substrate has the advantage of being both relatively inexpensive as a carbon source (Nakamura and Whited 2003) and easily transported into the cell, but it has the disadvantage of being readily consumed for normal cellular metabolism. Some consumption of carbon-containing substrates is necessary to generate the biomass, especially the enzymes, that provide the biocatalytic capacity of a fermentation process. However, it can have a significant impact on the carbon yield of final product (Chotani et al. 2000). While one might consider attempting to engineer an organism to consume a different carbon source for endogenous metabolism and "reserve" glucose for the recombinant pathway of interest, such an approach is confounded by the fact that glucose is a preferred substrate for *E. coli*. The requirement for two specified carbon sources, one of which may be more expensive than glucose, would also complicate the bioprocess configuration of a production system. Instead, described herein is a mechanism by which glucose can be diverted from endogenous metabolism towards heterologous pathways, leading to increased production of glucaric acid. The proposed Glucose Valves operate by first, altering glucose transport, then inhibiting phosphorylation to prevent entry into glycolysis and the pentose phosphate pathway (FIG. 2).

Glucose transport is altered by knocking out the phosphoenolpyruvate (PEP)-dependent glucose-phosphotransferase system (PTS). Glucose that enters through the PTS system is phosphorylated with the consumption of PEP, while in PTS knock-outs, glucose enters in an un-phosphorylated state and is subsequently modified by glucokinase (glk), with transfer of the terminal phosphate from ATP (Curtis and Epstein 1975). Strains deficient in both PTS systems and glucokinase are unable to grow on glucose. The PTS system has been a target of metabolic engineering in *E. coli*, especially to improve the synthesis of aromatics by de-coupling glucose transport and PEP consumption (Gosset 2005). PTS mutants exhibit significantly altered growth and metabolic profiles (Chen et al. 1997). Growth recovery is achieved with over-expression of either the endogenous galactose-proton symporter (galP) (Flores et al. 1996; Hernandez-Montalvo et al. 2003; De And a et al. 2006) or the glucose facilitator protein (glf) from *Zymomonas mobilis* (Snoep et al. 1994; Weisser et al. 1995). Using strains with altered glucose transport, yields of aromatic compounds derived from shikimic acid were improved by ≥40% (Yi et al. 2003). The sequence of the *Zymomonas mobilis* glf gene corresponds to GenBank Accession No. M60615/M37982, and is included below.

The ability to import glucose into the cytoplasm in a non-phosphorylated state represents an opportunity to divert the molecule from endogenous metabolism, which requires phosphorylation, towards alternative pathways, including those proposed for the synthesis of glucaric acid. Following the central dogma of molecular biology, glucokinase activity can be affected at the level of transcription by targeting the DNA, at translation by targeting the RNA, or by targeting the protein through post-translational means. Post-translational modulation presumes the availability of an inhibitor of the enzyme or a means of de-stabilizing and/or denaturing the folded polypeptide. On the other hand, control at the level of transcription and translation only requires knowledge of the gene sequence. One or more of these processes is targeted in the processes described herein for valve construction.

At the transcriptional level, a natural method for controlling glk expression would be through the use of a titratable promoter. While such promoters are well-known and readily available to titrate gene expression upwards in response to the addition of external effectors, here, the task is to regulate gene expression downwards such that glk expression is decreased when the valve is opened. We are currently unaware of promoters that respond negatively in such a titratable fashion, and removal of a positively-activating inducer is not scalable. However, an alternative is to replace the native promoter of glk with a repressible promoter (e.g., the Tet, Lac, or lambda promoter) and to place control of the corresponding repressor protein (e.g., TetR, LacI, or cI) under the control of a promoter that can in turn be activated. In such a system, the default state would be constitutive expression of glk, and addition of an external effector (the inducer) would result in down-regulation of glk expression. Such a device has been termed a genetic "inverter" since output (in this case, glk expression) is high when the input concentration (the effector molecule) is low, and the output is low when the input concentration is high (Registry of Standard Biological Parts, partsregistry.org). Thus, one version of the Glucose Valve can be implemented using an inverter.

At the level of translational control, down-regulate glk activity and diversion of glucose flux can be achieved through the use of antisense RNA (asRNA). asRNA transcripts were first observed in microbial systems and typically function by inhibiting translation of a sense messenger RNA template (Wagner and Simons 1994; Good 2003). In engineered microbial systems, asRNA has been used to probe gene function in cases where a knock-out may be lethal, and particularly for the study of virulent organisms (Kernodle et al. 1997; Wilson et al. 1998; Ji et al. 1999; Ji et al. 2001; Wang and Kuramitsu 2005). asRNA technology has been applied in metabolic engineering and analysis as well. In what appears to be the earliest example, asRNA was used to elucidate the role of a hydrogenase enzyme in lactate metabolism in *Desulfovibrio vulgaris* (Van den Berg et al. 1991). Strain alterations have been made to improve protein production by down-regulating both transcription factors to restrict protease synthesis (Srivastava et al. 2000) and enzymes in acetate metabolism to reduce secretion of this metabolite into fermentation broth (Kim and Cha 2003). The most extensive use of asRNA for metabolic engineering has been applied in *Clostridium acetobutylicum* (Desai and Papoutsakis 1999; Tummala et al. 2003; Tummala et al. 2003). In these examples, enzyme activities were reduced by as much as 86%, while butanol production was improved by nearly 3-fold. Efforts were also made to determine the structural features that led to the greatest impact of asRNA on knock-down of enzyme activity (Tummala et al. 2003).

Whether employing a repressor to affect transcription or an antisense RNA molecule to affect translation, controlled expression should enable fast growth and biomass production under non-induced conditions (closed valve) while induced expression will down-regulate glucokinase, decrease phosphorylation of glucose and divert it from endogenous metabolism towards product synthesis (open valve). This technology is attractive because it allows time-dependent, controlled decoupling of growth from product formation, a technique that has been used with great success to produce large quantities of recombinant proteins (Makrides 1996). Such valves are not expected to be 100% efficient in diverting glucose. Indeed, the leakiness of repressed promoters is well-known (Baneyx 1999; Keasling 1999), and the ability of asRNA to down-regulate enzyme activity has ranged from a low of 10% (Kim and Cha 2003) to a high of 98% (Pestka et al. 1984). While the efficiency of a particular asRNA transcript cannot be predetermined, its effectiveness is a function of its structure, and opportunities for optimization exist. It is expected to ultimately observe behaviors similar to those encountered with recombinant protein production (Dong et al. 1995), namely a significant reduction in the growth rate as a result of opening the valve, that is accompanied by a significant increase in product formation rates. While the data described herein relates to glucose in *E. coli*, the valve concept can be extended both to other metabolites and other organisms.

```
Sequence of Zymomonas mobilis glf gene (SEQ ID NO: 1):
atgagttctgaaagtagtcagggtctagtcacgcgactagccctaatcgctgctataggcggcttgcttttcggt tacgattcagcggttatcgctgcaatcggtacaccggttgatatccattttattgccctcgtcacctgtctgct acggctgcggcttccctttctgggatggtcgttgttgctgttttggtcggttgtgttaccggttctttgctgtct ggctggattggtattcgcttcggtcgtcgcggcggattgttgatgagttccatttgtttcgtcgccgccggtttt ggtgctgcgttaaccgaaaaatttatttggaaccggtggttcggctttacaaattttttgcttttccggtttctt gccggtttaggtatcggtgtcgtttcaaccttgaccccaacctatattgctgaaattcgtccgccagacaaacgt ggtcagatggtttctggtcagcagatggccattgtgacgggtgctttaaccggttatatctttacctggttactg gctcatttcggttctatcgattgggttaatgccagtggttggtgctggtctccggcttcagaaggcctgatcggt attgccttcttattgctgctgttaaccgcaccggatacgccgcattggttggtgatgaagggacgtcattccgag gctagcaaaatccttgctcgtctggaaccgcaagccgatcctaatctgacgattcaaaagattaaagctggcttt gataaagccatggacaaaagcagcgcaggtttgtttgcttttggtatcaccgttgttttgccggtgtatccgtt gctgccttccagcagttagtcggtattaacgccgtgctgtattatgcaccgcagatgttccagaatttaggtttt ggagctgatacggcattattgcagaccatctctatcggtgttgtgaacttcatcttcaccatgattgcttcccgt gttgttaccgcttcggccgtaaacctctgcttatttggggtgctctcggtatggctgcaatgatggctgtttta ggctgctgtttctggttcaaagtcggtggtgttttgcctttggcttctgtgcttctttatattgcagtctttggt atgtcatgggccctgtctgctgggttgttctgtcagaaatgttcccgagttccatcaagggcgcagctatgcct atcgctgttaccggacaatggttagctaatatcttggttaacttcctgtttaaggttgccgatggttctccagca
```

```
ttgaatcagactttcaaccacggtttctcctatctcgttttcgcagcattaagtatcttaggtggcttgattgtt gctcgcttcgtgccggaaaccaaaggtcggagcctggatgaaatcgaggagatgtggcgctcccagaagtag
```

Example 2

Construction of an E. Coli Strain with Altered Glucose Transport

Whether the Glucose Valve is implemented at the level of transcription or translation, the first step in the construction process was to engineer a host strain with altered glucose transport. A PTS-deficient mutant of the commonly used E. coli laboratory strain DH10B was constructed by knocking-out the ptsHI-crr operon utilizing the method of Datsenko and Wanner (Datsenko and Wanner 2000). Although previous reports indicated that a mutation in the glucose transporter (ptsG) alone was not sufficient to prevent good growth on glucose (Curtis and Epstein 1975), the components of the PTS system (ptsHI) that are required for phosphorylation of glucose even when lower affinity transporters such as that preferred by mannose (manXYZ) are left intact were targeted herein. The resulting strain, named KTS-002, was only capable of slow growth on M9 minimal medium with glucose as a sole carbon source and also exhibited a lag time of more than 2 days longer than the DH10B parent.

To restore a robust glucose-utilization phenotype to the strain, the native promoter of the endogenous galactose permease (galP) gene was replaced with the constitutive promoter from lacI$^q$ (MIT Registry of Standard Parts, parts.mit.edu, Part I 14032). This promoter replacement was also achieved using the Datsenko and Wanner method, resulting in strain KTS-022. In previous reports with PTS-deficient mutants, up-regulation of a permease increased growth rates to nearly 90% of the PTS-active parents, but concomitant over-expression of glucokinase was necessary to restore rates to equivalent levels (Hernandez-Montalvo et al. 2003; Gosset 2005). In experiments described herein, KTS-022 exhibited the same growth rate and reached the same cell densities as the DH10B parent strain. In fact, when the native promoter of the glk gene was replaced with the constitutive lacIq promoter, the growth rates were significantly decreased and the cultures failed to grow to a significant cell density ($OD_{600}$<0.1 after several days incubation). Without wishing to be bound by any theory, this result may have been due to the strength of the promoter.

Example 3

Design, Construction and Evaluation of Antisense Transcripts as Glucose Valves The construction of a translationally-controlled Glucose Valve was approached using antisense technology. While natural microbial antisense RNAs (asRNAs) vary in length from ~50 to ~200 nts (Good 2003), the lengths of engineered antisense transcripts targeted against specific genes have typically been much longer, ranging from ~150 (Kim and Cha 2003) to over 2500 nts (Ellison et al. 1985). Inverting the entire open reading frame has proven effective (Van den Berg et al. 1991), yet so has expressing just 38% of the inverted gene (Tummala et al. 2003). In some instances, the ribosome binding site (RBS) is included in the transcript (Good 2003). In other instances, down-regulation has been observed in the absence of an anti-RBS (Ellison et al. 1985). In some instances, a direct inversion of the open reading frame and 5' untranslated region appears effective, as attempts to design asRNA based on structural homology to natural antisense molecules have in some instances been unsuccessful (Engdahl et al. 1997).

The impact on down-regulation of enzyme activity as a result of the various implementations of engineered asRNA described in the literature has varied. Reductions in activity as low as 10% (Kim and Cha 2003) and as high as 98% have been reported (Pestka et al. 1984). Of note is one report that evaluated the effectiveness of related asRNAs based on length and structure (Tummala et al. 2003). This report concluded that highest inhibition is achieved with the lowest "component/nucleotide" ratio, where components are "structural features that contain regions of high complementarity within an asRNA molecule." In other words, components are segments of double-stranded RNA. This analysis was done with asRNA for Clostridium acetobutylicum, and the shortest asRNA transcripts were still larger than 500 nts. It is unclear if the same relationship is true for E. coli or other microbial organisms.

Figure 3:
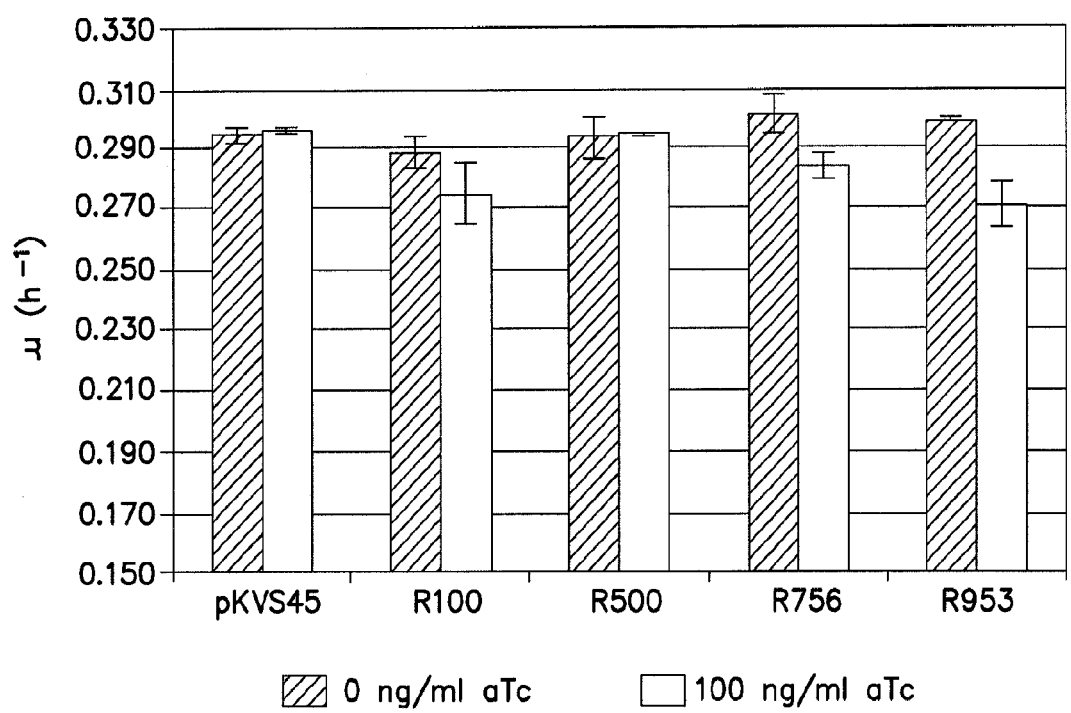
FIG. 3 presents a graph demonstrating the effect of asRNA expression on KTS-022 growth rate in the presence (right bar in each set of bars) and absence (left bar in each set of bars) of aTc inducer.

Four asRNA transcripts targeted against E. coli glucokinase were designed and constructed. The glk open reading frame is 966 bp, and the asRNA transcripts were designed to comprise ~10% (100 nts), ~50% (500 nts), ~75% (756 nts), and >95% (953 nts) of the open reading frame, in addition to the RBS. The asRNA sequences were cloned into a vector under the control of the $P_{tet}$ promoter, inducible with the addition of anhydrotetracycline (aTc). As an initial evaluation of the performance of the transcriptionally-controlled valves, strain KTS-022 was transformed with each of the four asRNA vectors and growth rates with and without aTc were measured and compared to the empty vector control (FIG. 3). If the valve is effective, glucokinase down-regulation is expected to reduce glucose utilization and slow growth. The control vector showed no difference in growth rate between cells with and without aTc, while three of the 4 asRNA samples appear to show a difference in growth rate following induction. In particular, the difference in growth rate for R953, appeared to be significant.

Figure 4:
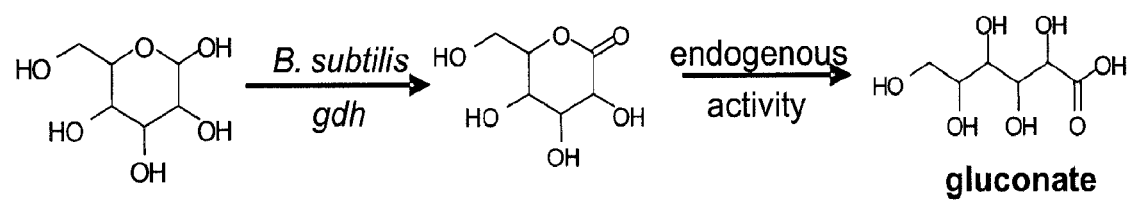
FIG. 4 presents a schematic depicting production of gluconate from glucose through glucose dehydrogenase. Gluconate is an intermediate in a proposed pathway towards glucaric acid.

Gluconate production was used to assess the effectiveness of the asRNA effect. Gluconate can be produced from un-phosphorylated glucose by glucose dehydrogenase (gdh). Herein gdh from Bacillus subtilis was used (EC 1.1.1.47, GenBank Accession Number M12276). Gluconate also serves as an intermediate in an alternative pathway towards glucaric acid (FIG. 4). Thus, a significant improvement in flux towards gluconate is a promising step towards developing a system that could be effective in glucaric acid production. KTS-022 was transformed with a vector containing the R953 asRNA construct, and a second vector harboring the B. subtilis gdh gene. Cultures were grown in M9 minimal medium with glucose as the sole carbon source, both genes were induced, and gluconate content was measured at 24 hours. The specific productivity of the R953 sample with inducer was 3-fold higher than the same sample without inducer (0.12 g-gluconate/OD-unit vs. 0.041 g/OD) and was 7-fold higher than the no-asRNA control (0.017 g/OD). As anticipated, the R953 strains also grew more slowly and at 24-hrs, had only reached a cell density equal to $\frac{1}{6}^{th}$ that of the control strain. The molar yield of gluconate on glucose was 2.5-fold higher for the induced R953 culture relative to the uninduced culture, and was 5-fold higher than the control.

Figure 5:
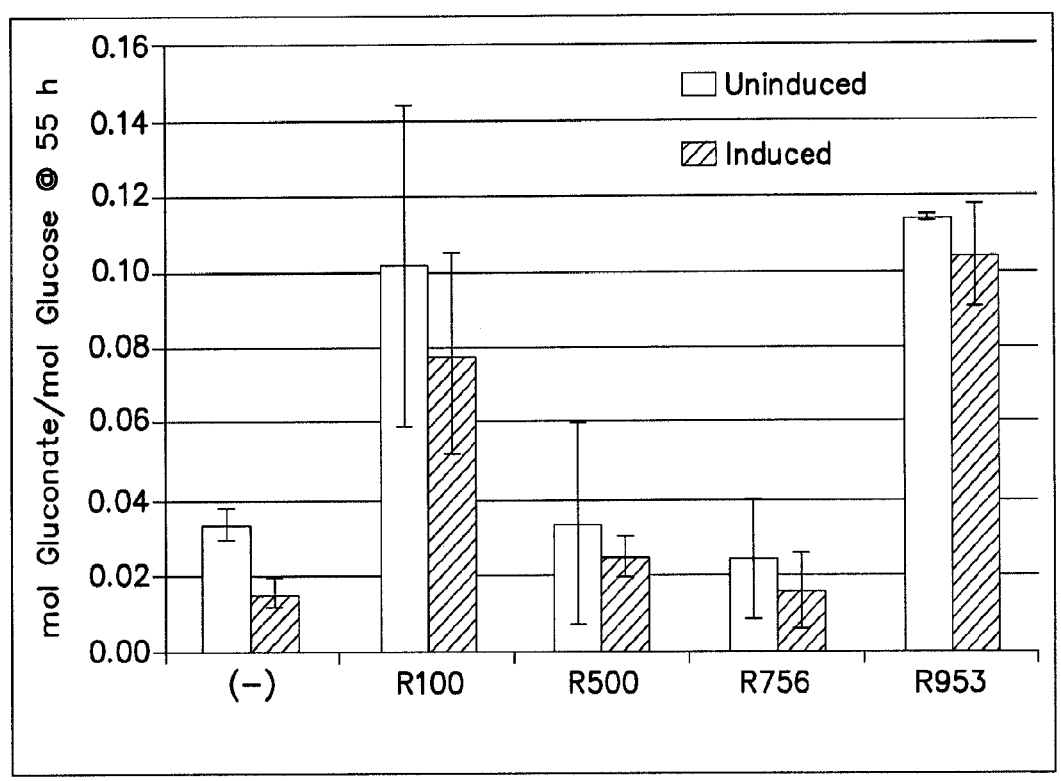
FIG. 5 presents a graph showing mol of gluconic acid produced per mol of glucose consumed in KTS022 at 55 h with delayed antisense induction; results are depicted for presence (right bar in each set of bars) and absence (left bar in each set of bars) of aTc inducer. All strains contain pKVS45 with the indicated antisense construct within the MCS. All strains also contain and express gdh from pTrc99 Cm induced with 0.1 mM IPTG at inoculation. Antisense was induced with 100 ng/ml aTc at 36 h as indicated. All strains were grown in M9 (1.5% Glu) supplemented with 0.8 mM L-leucine

In other experiments, in the presence of R953, gluconate specific productivity increased 8-fold relative to aTc-induced empty vector controls and 3 fold relative to uninduced R953 vector. Repeating the experiment with 1.5% glucose, titers in excess of 1 g/L were observed for R100 and R953 with specific productivity increases of ~20-fold for uninduced cultures and 5-fold for induced cultures. FIG. 5 shows the gluconate yield per mol glucose in KTS-022. While the trend for induced vs uninduced is counterintuitive for 1.5% glucose, it would be consistent with limiting cofactor regeneration rates at higher glucose levels and reduced glycolytic rates. Nonetheless, in both cases, the presence of antisense was able to shift the glucose away from glycolysis towards gluconate formation resulting in higher specific productivities.

Thus, these results indicate successful design and construction of an effective first generation Glucose Valve.

Materials and Methods

Strains and Plasmids

To construct the antisense RNA, fragments of glk (Genbank Accession no. ECK2384) were PCR amplified using a pair of forward and reverse primers as described in Table 1.

Analytics

Gluconate titers were estimated either enzymatically or through HPLC analysis. At ~24 and ~48 h after inoculation, 1 ml samples were taken and clarified by centrifugation for 2 mM at 16 000 g. For enzymatic analysis, the supernatant was diluted 3-fold before being assayed with the gluconate assay kit from Megazayme (Bray, Ireland) where gluconate is phosphorylated and then reduced to generate a NADH signal that is detected spectrophotometrically. Alternatively, the samples were measured in an HPLC assay using an Agilent 1100 Series instrument equipped with a Bio-Rad Aminex HPX-87H chromatography column. The mobile phase used was 5 mM sulfuric acid at a flowrate of 0.60 mL min$^{-1}$ The column was maintained at a temperature of 55° C. and an Agilent 1100 series diode array detector (DAD) at 230 nm and refractive index (RI) detector were used for the detection of gluconate and glucose. Under these conditions, gluconate and glucose co-elute at ~8.9 mM, however, glucose does not absorb UV at 230 nm. Both methods agree on gluconate quantification within 15%.

TABLE 1

Primer pairs used to construct glk antisense fragments

| Construct | SEQ ID | Primer | Direction | | Homology | Amplicon |
|---|---|---|---|---|---|---|
| | 4 | glk as rev -20 | Forward | CTAT GTCGACGATATC | TTTAGCGGAGCAGTTGAAGA | |
| R100 | 5 | glk as for 100 | Reverse | CTAT GAATTC | AATAGGTCTTAGCCTGCGAG | 149 nts |
| R500 | 6 | glk as for 500 | Reverse | CTAT GAATTC | CTATTCGGCGCAAAATCAAC | 549 nts |
| R756 | 7 | glk as for 756 | Reverse | CTAT GAATTC | GAGATTGAGCGCCAGATTG | 805 nts |
| R953 | 8 | glk as for 953 | Reverse | CTAT GAATTC | CCTAAGGTCTGGCGTAAATG | 1002 nts |

Restriction sites are underlined

These fragments were then cloned into plasmid pKVS45, constructed from the pBAD30[6] backbone and tet-induction system from pWW308 (provided by Dr. Deuber, UCB), using the restriction sites indicated. To test the effectiveness of redirecting glycolytic flux, glucose dehydrogenase[7] (Genbank Accession no. M12276), from *B. subtilis*, was amplified with the primers For_gdh_subtilis (TACATATAAG TCTAGATAACAAATGGAGGAGGATG; SEQ ID NO:2) and Rev_gdh_subtilis (CAAGTAACTA AAGCTTTCATGTCTGGGTCGCT; SEQ ID NO:3) and cloned into pTrc99 Cm, a pTrc99A derivative where bla (Amp$^R$) was disrupted with the insertion of cat (Cm$^R$), with the underlined restriction sites.

Culture Conditions and Results

KTS-022 (ΔptsHIcrr galpP$^q$) was transformed with pTrc99 Cm-gdh and each of the pKVS45 plasmids and grown in 5 ml minimal media (M9, 0.4% glucose, 0.8 mM leucine, 100 µM IPTG) at 37° C. to OD ~0.5. A 0.1% inoculum was transferred to fresh minimal media and grown under similar conditions and at OD ~0.5 were transferred to 50 ml minimal media where antisense was induced with 100 mg/ml aTC. gdh catalyzes the one step conversion of glucose into glucono-δ-lactone (gluconate) and competes directly with glk for glucose substrate.

Example 4

Characterization of the Strain with Native glk Promoter Disruption and Replacement Plasmids Plasmids used were as described above.

Strains

The antisense fragments described above were tested in KTS622 (DH10B ΔptsHIcrr galP$^q$ glk$^q$), a derivative of KTS022 (previously described, also referred to herein as KTS-022) with the regulatory FruR binding site of glk removed and the native promoter(s) of glk disrupted and replaced with J23117 from the Registry of Standard Biological Parts (partsregistry.org).

Culture Conditions and Results

Figure 6:
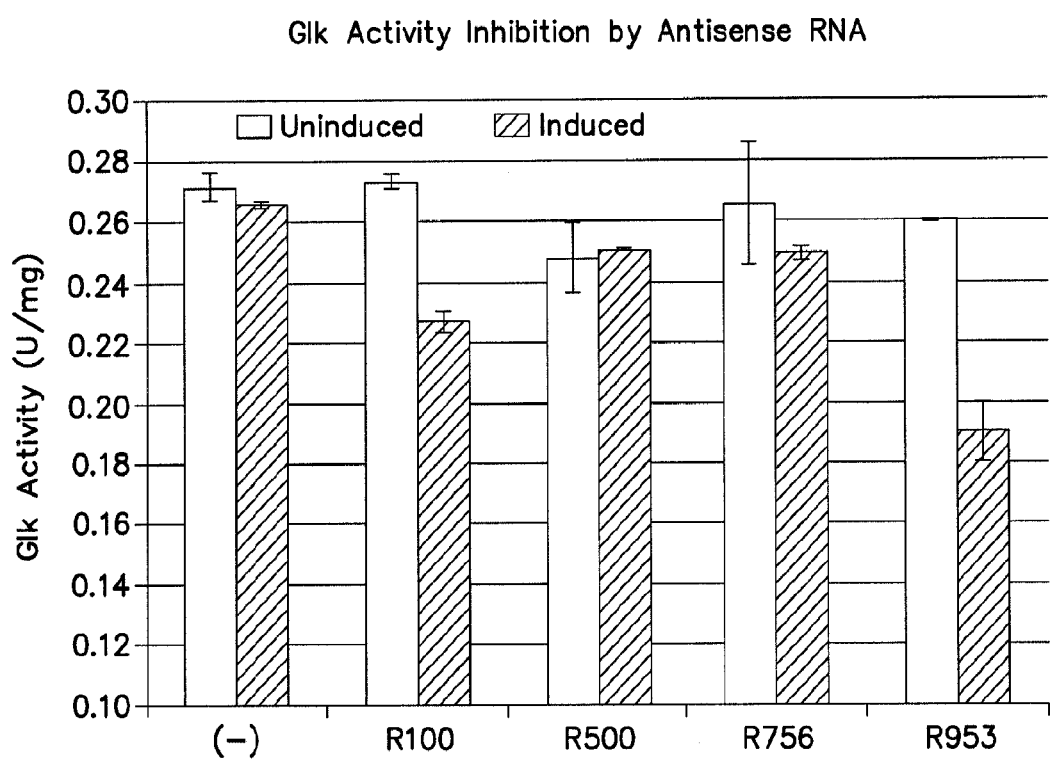
FIG. 6 presents a graph showing Glk activity repression by antisense RNA in KTS622 in the presence (right bar in each set of bars) and absence (left bar in each set of bars) of aTc inducer. All strains contain pKVS45 with an antisense RNA construct as indicated. Antisense RNA was induced with the 100 ng/ml aTc at inoculation (0.1% inoculum). All strains were grown in M9 (1.5% Glu) supplemented with 0.8 mM L-leucine. The activity was read from cells at mid exponential phase (OD ~0.5).
Figure 7:
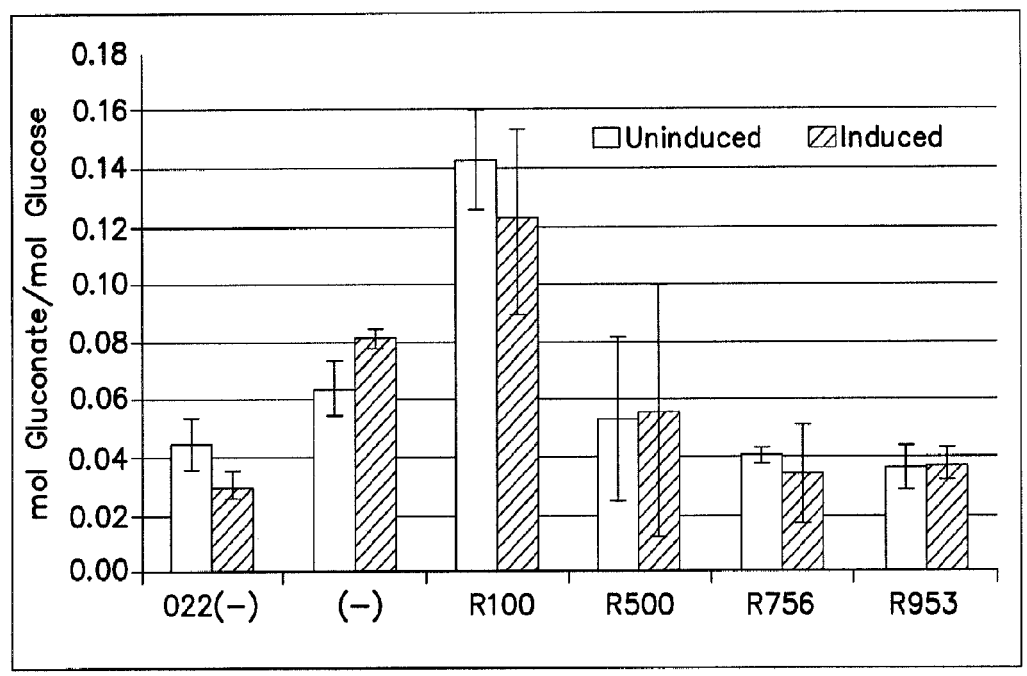
FIG. 7 presents a graph showing gluconate yield (mol) per mol glucose in KTS622 in the presence (right bar in each set of bars) and absence (left bar in each set of bars) of aTc inducer. 022(-) is a KTS022 control containing pKVS45 and (-) is an empty vector KTS622 control. All other strains are KTS622 containing pKVS45 with the indicated antisense construct within the MCS. All strains also contain and express gdh from pTrc99 Cm induced with 0.1 mM at inoculation. Antisense was induced with 100 ng/ml aTc at inoculation as indicated.

KTS622 was transformed with pTrc99 Cm-gdh and each of the pKVS45 plasmids and grown in 5 ml minimal media (M9, 1.5% glucose, 0.8 mM leucine, 100 µM IPTG) at 37° C. to early-mid exponential phase (OD 0.1-0.5). A constant cell number (1% inoculum max) was transferred to 4×50 ml fresh minimal media and grown under similar conditions. Two flasks of each series were supplemented with 100 ng/ml aTc to induce the antisense. Flasks were incubated for ~49 h before being assayed using an LC method as described previously. This data was compared with a KTS022 [pKVS45 pTrc99 Cm-gdh] control. Glucokinase activity was measured using an assay as described previously (e.g., Goward et al. 1986). FIG. 6 presents a graph showing Glk activity repression by antisense RNA in KTS622. FIG. 7 shows the results in mol of gluconic acid produced per mol of glucose consumed at 49 h.

Going from KTS022 to KTS622, there is a 50% improvement in gluconate molar yield due to the 12% decrease in glk activity. This effect is amplified with the introduction of the R100 antisense construct showing a 100% improvement relative to an empty vector KTS622 control and 3-fold relative to a KTS022 control. The other antisense constructs show negligible impact relative to a KTS622 control. Counterintuitively, induction of R100 shows no further improvement beyond leaky uninduced expression suggesting some system limitation beyond glk expression.

Example 5

Characterization of the Translationally-Controlled (asRNA-Mediated) Glucose Valve The translationally-controlled Glucose Valve was characterized with respect to mechanism of action and temporal effects.

Quantification of glk Sense and Antisense mRNA

The asRNA-mediated valves were designed to operate by producing transcripts complementary to the sense strand of glk that would hybridize and inhibit translation. The asRNA constructs were placed on a multi-copy plasmid to produce sufficient copies of the asRNA to promote hybridization, though a moderately low-copy plasmid with a p15A replicon (~10 copies per cell) was used to minimize the effects of background (i.e., "leaky") expression of the asRNA.

To further characterize this system, quantitative reverse transcriptase PCR (qRT-PCR) is used to quantify expression of the asRNA constructs. Sets of primers are designed that facilitate the measurement of both total glk RNA (both sense and antisense) and only the sense mRNA, based on sequences at the extreme 3' end in the sense direction that were omitted from the asRNA designs. Using this assay, the relative amounts of sense and antisense RNA can be quantified and it can be determined whether there is a correlation between antisense/sense ratio and the function of the valve.

qRT-PCR is also used to determine whether antisense expression contributes to the instability of the sense transcripts, as has been reported (Srivastava et al. 2000). Primers designed to amplify multiple regions of the transcript are used to assess stability.

In the experiments described above, a single aTc concentration was examined. Yet, one advantage of the valve design is the ability to modulate the degree to which the valve is "open," either through structural differences in the asRNA transcripts that impact the hybridization effectiveness, or through titration of the levels of asRNA. As was observed in the gluconate production experiment, a fully open valve suffers from a reduced growth rate, diverting substantial flux from endogenous metabolism. However, the effect of this diversion on asRNA levels is unknown. Transcript levels from the four asRNA constructs with respect to induction level are measured to determine whether the effectiveness of the asRNA constructs is related to the inducer concentration.

Measurement of Glucokinase Activity

The translationally-controlled valve is designed to act through asRNA and reduce glucokinase activity. Hence, characterization of the valves' effects involves quantification of the target enzyme activity. Glucokinase activity is measured using assays that have been described previously (Goward et al. 1986). This measurement is used to quantify the extent of down-regulation relative to control cultures that do not contain the asRNA transcripts (no valve) and to those with uninduced asRNA expression (closed valve).

Characterization of the Temporal Effects of the Valve

In the data presented in FIG. 3, growth rates were determined in response to a single inducer concentration added to the culture at a single time point. The induction time (at the point of inoculation) was chosen to maximize the potential effect of the constructs. In order to optimize the level of induction and timing of induction to maximize valve effectiveness, measurements of asRNA, sense RNA, and glucokinase activity are made as described previously as a function of time to understand the dynamic response of the system. These data feed into a mathematical model discussed below that defines the parameter space over which an asRNA valve is effective.

Example 6

Design, Construction and Characterization of a Transcriptionally-Controlled (Repressor-Mediated) Glucose Valve A transcriptionally-controlled Glucose Valve is also designed and constructed. This valve design is based on a genetic inverter, in which the native promoter of glk is replaced with a repressible promoter, and the gene encoding the corresponding repressor is then placed under the control of an inducible promoter. Functionality of the repressor-mediated valve is evaluated in a manner similar to that described for the asRNA-mediated device described above.

Establishment of an Operating Window for Constitutive Expression of Glk

Replacement of the native glk promoter with the constitutive lacI$^q$ promoter in KTS-022 resulted in a strain severely comprised in growth on glucose as a sole carbon source. At the same time, a glk knock-out of KTS-022 is expected to be incapable of growth on glucose (Curtis and Epstein 1975). Thus, a range of expression levels can be established that approximates the minimum level to support growth and the maximum level to prevent growth inhibition. This is achieved by utilizing several members of a family of constitutive promoters that are structurally similar (with respect to sequence length) but which vary in strength. Two such families have been reported, one based on the lambda promoter (Alper et al. 2005), and the other derived from the sigma-70 consensus sequence from E. coli promoters (J. C. Anderson's Promoter Library, 2006 Berkeley iGEM Team, partsregistry.org). Both libraries cover a two-order of magnitude range in activity, but it is not clear how these ranges overlap, if they do so at all.

Five promoter sequences are selected covering the 100-fold range of strengths previously reported from each library, KTS-022 derivatives are constructed with constitutively expressed glk for each promoter variant and resulting growth rates are determined The genomic promoter replacements are accomplished using the Datsenko and Wanner method, as previously described for the construction of the constitutively expressed galP mutation to construct KTS-022. The qRT-PCR primers designed previously to amplify the sense transcript are used to measure the glk mRNA levels as a function of promoter construct and determine the correlation between mRNA levels and growth rate.

Replacement of Native glk Promoter with an Inverter Device

The first step in the design of the inverter is to determine the promoter under which glk should be expressed. The second component of the inverter is the placement of the repressor protein under the control of a separate, inducible promoter. One such inverter is defined in the Registry of Standard Biology Parts (partsregistry.org, Part BBa_J5516). Utilization of this inverter design replaces the glk promoter with the lambda promoter. Adjacent to the promoter is a LacI operator site, enabling repression by LacI. Thus, the lacI gene is incorporated upstream, in this example, under the control of the arabinose-inducible $P_{BAD}$ promoter. Addition of arabinose in the presence of the AraC activator/repressor protein should result in expression of the LacI repressor protein and down-regulation of glk expression.

A promoter can then be directly modified by the addition of, for example, a LacI operator site to introduce the ability to repress expression. One consideration for the use of arabinose induction is catabolite repression and the need for glucose in the experimental system. Arabinose induction is usually ineffective in the presence of glucose; however, the removal of the PTS transporter has been shown to alleviate catabolite repression (Gosset 2005). In our studies, we have found arabinose induction to occur in KTS-022 with glucose as the sole carbon source, however, the response time is very long. To retain the same effector molecule used in the asRNA-mediated valve, the lad repressor gene can be placed under the control of the aTc-inducible $P_{tet}$ promoter, repressed by the TetR repressor. Thus, in the absence of aTc, LacI repressor concentration should be low and glk expression should be high. Upon addition of aTc, LacI repressor concentration should increase, causing a correlative decrease in glk expression and, ultimately, glucokinase activity.

In order to select and/or optimize a promoter that will yield a healthy KTS-022 derivative, the ability to successfully modify the chosen sequence with an operator site for a repressor is verified by establishing that glucokinase activity in the absence of induction of the repressor remains high and determining that repression is effective in the presence of the inducer.

Implementing this portion of the device can involve some sequence optimization as the separate parts are functionally assembled together. Testing of device configurations is accomplished macroscopically by examining the effect on growth rate with and without inducer.

Example 7

Characterization of the Inverter (Repressor-Mediated) Glucose Valve

The transcriptionally-controlled inverter valve is characterized using the same set of tools and experiments as described above for the asRNA system. Measurements of mRNA levels are made to determine the degree and temporal nature of repression of glk expression, and glucokinase activity is measured to evaluate the extent of down-regulation of the enzyme. Use of the qRT-PCR assay for mRNA measurements is simplified by the absence of complementary antisense transcripts in this valve design. The system is also employed to determine the effect on growth (a macroscopic property) and productivity of the gluconate model system. Finally, the dynamics of the system are determined, both to incorporate into a model of the Valve's performance and to compare its effectual parametric space with that determined from the asRNA-mediated system.

Example 8

Development of Mathematical Models to Describe and Design Metabolite Valves

A goal of this work is to establish a design methodology that facilitates the design and construction of a valve for any metabolite. To this end, the system is mathematically described and the governing design equations are developed for metabolite valves.

Intuitively, one might assume that the effectiveness of any valve must be a function of the half-life of the protein whose activity is being targeted. This is evident from the fact that both manifestations of the valve prevent the synthesis of new protein molecules but do not affect the activity of existing proteins. Hence, a very stable protein is likely to require a very long response time to observe a decrease in activity while a system based on a protein with a very fast turnover rate should respond more quickly. Qualitatively, this prediction is fairly straightforward; however, a goal is to understand the quantitative impact of, for example, alterations in the half-life of the target protein. The ability to define the parameter space over which we expect the system to respond in a "reasonable" timeframe (where, "reasonable" must be defined by the user) serves two purposes. First, it enables a prediction of whether a designed valve will actually be effective. Secondly, and certainly as importantly, a robust model can identify parameters that may be amenable to alteration in order to enable effective operation of the device. For example, ssrA degradation tags can be added to the peptide sequence in order to promote degradation and reduce the half-life of the target protein (Karzai et al. 2000).

Figure 8:
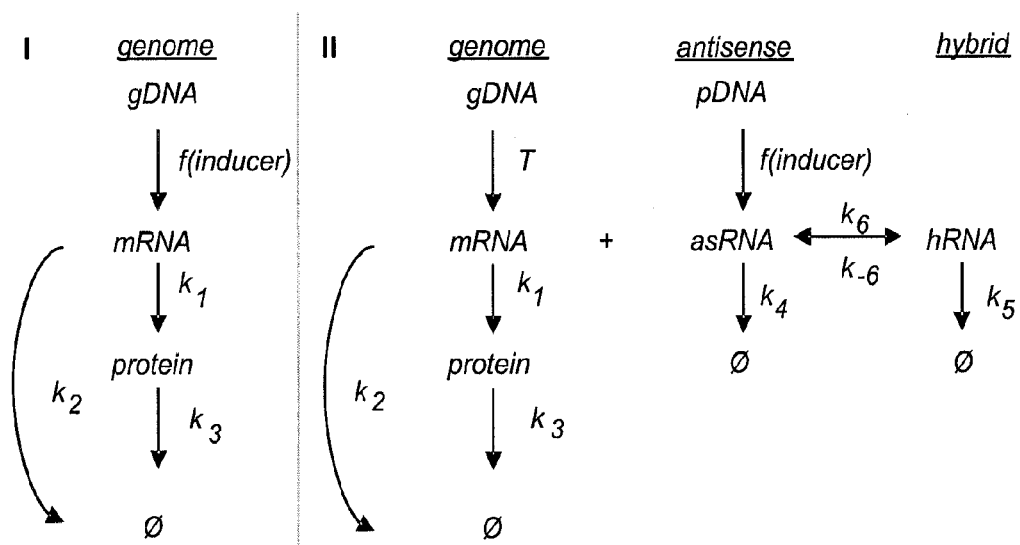
FIG. 8 presents a schematic showing models for transcriptionally-controlled (I) and translationally-controlled (II) Metabolite Valves. In (I), mRNA levels are a function of inducer, while in (II) asRNA levels are a function of inducer. "Ø" represents non-functional degradation products of either RNA or protein.

As a first effort, first-order ODE models with a mass action framework are used to describe the functioning of the various valves (FIG. 8; Levine et al. 2007; Shimoni et al. 2007). The repressor-mediated (transcriptionally-controlled) system is relatively straight-forward to model, assuming first order kinetics for mRNA and protein synthesis and decay, dilution by growth, and accounting for the induction effect as a decrease in the synthesis rate of mRNA. The asRNA-mediated (translationally-controlled) system has the same first order assumptions, but must now account for the first-order production of asRNA and subsequent hybridization. Hybrids are assumed to be incapable of translation, but the model may assume that hybridization is reversible. This system is subsequently more complex. The values of the model parameters are extractable from the experimental data, especially from measurements of sense and antisense mRNA, and glucokinase activities as a function of both inducer concentration and time. In instances where it is not possible to extract the parameters, representative values are chosen (for example, for transcription and translation rates) from the literature. The goal is to develop a mathematical description of the valves that will enable optimal design and implementation of the Glucose Valve and that will facilitate design of new Metabolite Valves.

REFERENCES

Alper, H., C. Fischer, E. Nevoigt and G. Stephanopoulos (2005). "Tuning genetic control through promoter engineering." *PNAS* 102(36): 12678-12683.

Bailey, J. E. (1991). "Toward a science of metabolic engineering." *Science* 252: 1668-1675.

Baneyx, F. (1999). "Recombinant protein expression in *Escherichia coli*." *Curr. Opin. Biotechnol.* 10: 411-421.

Bommarius, A. S, and K. M. Polizzi (2006). "Novel biocatalysts: recent developments." *Chem. Eng. Sci.* 61(3): 1004-1016.

Chen, R., W. M. G. J. Yap, P. W. Postma and J. E. Bailey (1997). "Comparative studies of *Escherichia coli* strains using different glucose uptake systems: metabolism and energetics." *Biotechnol. Bioeng.* 56(5): 583-590.

Chotani, G., T. Dodge, A. Hsu, M. Kumar, R LaDuca, D. Trimbur, W. Weyler and K. Sanford (2000). "The commercial production of chemicals using pathway engineering." *Biochim. Biophys. Acta* 1543: 434-455.

Curtis, S. J. and W. Epstein (1975). "Phosphorylation of D-glucose in *Escherichia coli* mutants defective in glucosephosphotransferase, mannosephosphotransferase, and glucokinase." *J. Bacteriol.* 122(3): 1189-1199.

Datsenko, K. A. and B. L. Wanner (2000). "One-step inactivation of chromosomal genes in *Escherichia coli* K-12 using PCR products." *PNAS* 97(12): 6640-6645.

De Anda, R., A. R. Lara, V. Hernandez, V. Hernandez-Montalvo, G. Gosset, F. Bolivar and O. T. Ramirez (2006). "Replacement of the glucose phosphotransferase transport system by galactose permease reduces acetate accumulation and improves process performance of *Escherichia coli* for recombinant protein production without impairment of growth rate." *Metabolic Eng.* 8: 281-290.

Desai, R. P. and E. T. Papoutsakis (1999). "Antisense RNA strategies for metabolic engineering of *Clostridium acetobutylicum*." *Appl. Environ. Microbiol.* 65(3): 936-945.

Dong, H., L. Nilsson and C. G. Kurland (1995). "Gratuitous overexpression of genes in *Escherichia coli* leads to growth inhibition and ribosome destruction." *J. Bacteriol.* 177(6): 1497-1504.

Ellison, M. J., R. J. Kelleher and A. Rich (1985). "Thermal regulation of β-galactosidase synthesis using antisense RNA directed against the coding portion of the mRNA." *J. Biol. Chem.* 260(16): 9085-9087.

Engdahl, H. M., T. A. H. Hjalt and E. G. H. Wagner (1997). "A two unit antisense RNA cassette test system for silencing of target genese." *Nucleic Acids Res.* 25(16): 3218-3227.

Farmer, W. R. & Liao, J. C. Improving lycopene production in *Escherichia coli* by engineering metabolic control. *Nature Biotechnology* 18, 533-537 (2000).

Flores, N., J. Xioa, A. Berry, F. Bolivar and F. Valle (1996). "Pathway engineering for the production of aromatic compounds in *Escherichia coli*." *Nat. Biotechnol.* 14: 620-623.

Good, L. (2003). "Translation repression by antisense sequences." *Cell. Mol. Life. Sci.* 60: 854-861.

Gosset, G. (2005) "Improvement of *Escherichia coli* production strains by modification of the phosphoenolpyruvate: sugar phosphotransferase system." *Microbial Cell Factories* 4: Art No. 14.

Goward, C. R., R. Hartwell, T. Atkinson and M. D. Scawen (1986). "The purification and characterization of glucokinase from the thermophile *Bacillus stearothermophilus*." *Biochem. J.* 237: 415-420.

Guzman, L. M., Belin, D., Carson, M. J. & Beckwith, J. Tight regulation, modulation, and high-level expression by vectors containing the arabinose PBAD promoter. *J Bacteriol* 177, 4121-30 (1995).

Hernandez-Montalvo, V., A. Martinez, G. Hernandez-Chavez, F. Bolivar, F. Valle and G. Gosset (2003). "Expression of galP and glk in an *Escherichia coli* PTS mutant restores glucose transport and increases glycolytic flux to fermentation products." *Biotechnol. Bioeng.* 83(6): 687-694.

Ji, Y., A. Marra, M. Rosenberg and G. Woodnutt (1999). "Regulated antisense RNA eliminates alpha-toxin virulence in *Staphylococcus aureus* infection." *J. Bacteriol.* 181(21): 6585-6590.

Ji, Y., B. Zhang, S. F. Van Horn, P. Warren, G. Woodnutt, M. K. R. Burnham and M. Rosenberg (2001). "Identification of critical staphylococcal genes using conditional phenotypes generated by antisense RNA." *Science* 293: 2266-2269.

Jiang, L., E. A. Althoff, F. R. Clemente, L. Doyle, D. Rothlisberger, A. Zanghellini, J. L. Gallaher, J. L. Betker, F. Tanaka, C. F. B. III, D. Hilvert, K. N. Houk, B. L. Stoddard and D. Baker (2008). "De novo computational design of retro-aldol enzymes." *Science* 319: 1387-1391.

Kapil, G. G., Francis, J. D., III, Jeremy, S. E. & Radhakrishnan, M. Estimating optimal profiles of genetic alterations using constraint-based models. *Biotechnology and Bioengineering* 89, 243-251 (2005).

Karzai, A. W., E. D. Roche and R. T. Sauer (2000). "The SsrA-SmpB system for protein tagging, directed degradation and ribosome rescue." *Nat. Struct. Biol.* 7(6): 449-455.

Keasling, J. D. (1999). "Gene-expression tools for the metabolic engineering of bacteria." *TIBTECH* 17: 452-460.

Kernodle, D. S., R. K. R. Voladri, B. E. Menzies, C. C. Hager and K. M. Edwards (1997). "Expression of an antisense hla fragment in *Staphylococcus aureus* reduces alpha-toxin production in vitro and attenuates lethal activity in a murine model." *Infect. Immun.* 65(1): 179-184.

Kiely, D. E., L. Chen and T. H. Lin (1994). "Simple preparation of hydroxylated nylons—polyamides derived from aldaric acids." *ACS Sym. Ser.* 575: 149-158.

Kim, J. Y. H. and H. J. Cha (2003). "Downregulation of acetate pathway through antisense strategy in *Escherichia coli*: improved foreign protein production." *Biotechnol. Bioeng.* 83(7): 841-853.

Kuellmer, V. (2001, April 2001). "Ascorbic acid." *Kirk-Othmer Encyclopedia of Chemical Technology* 4th. from http://mrw.interscience.wiley.com/emrw/9780471238966/home/.

Lampel, K. A., Uratani, B., Chaudhry, G. R., Ramaley, R. F. & Rudikoff, S. Characterization of the developmentally regulated *Bacillus subtilis* glucose dehydrogenase gene. *J Bacteriol* 166, 238-43 (1986).

Lee, Lee, P., Schmidt, D. & Schmidt-Dannert, C. Metabolic engineering towards biotechnological production of carotenoids in microorganisms. *Applied Microbiology and Biotechnology* 60, 1-11 (2002).

Leonard, E., D. R. Nielsen, K. V. Solomon and K. L. J. Prather (2008). "Engineering microbes with synthetic biology frameworks." *Trends Biotechnol.* 26(12): 674-681.

Levine, R., Z. Zhang, T. Kuhlman and T. Hwa (2007). "Quantitative characteristics of gene regulation by small RNA." *PLoS Biol.* 5: e229.

Lippow, S. M. and B. Tidor (2007). "Progress in computational protein design." *Curr. Opin. Biotechnol.* 18: 305-311.

Makrides, S. C. (1996). "Strategies for achieving high-level expression of genes in *Escherichia coli*." *Microbiol. Rev.* 60(3): 512-538.

Mijts, B. N. and C. Schmidt-Dannert (2003). "Engineering of secondary metabolite pathways." *Curr. Opin. Biotechnol.* 14: 597-602.

Nakamura, C. E. and G. M. Whited (2003). "Metabolic engineering for the microbial production of 1,3-propanediol." *Curr. Opin. Biotechnol.* 14: 454-459.

Nielsen, J. (2001). "Metabolic engineering." *Appl. Microbiol. Biotechnol.* 55: 263-283.

Pestka, S., B. L. Daugherty, V. Jung, K. Hotta and R. K. Pestka (1984). "Anti-mRNA: specific inhibition of translation of single mRNA molecules." Proc. Natl. Acad. Sci. USA 81: 7525-7528.

Pfeifer, B. A., S. J. Admiraal, H. Gramajo, D. E. Cane and C. Khosla (2001). "Biosynthesis of complex polyketides in a metabolically engineered strain of E. coli." Science 291: 1790-1792.

Pfeifer, B. A., C. C. C. Wang, C. T. Walsh and C. Khosla (2003). "Biosynthesis of yersiniabactin, a complex polyketide-nonribosomal peptide, using Escherichia coli as a heterologous host." Appl. Environ. Microbiol. 69(11): 6698-6702.

Ro, D.-K., E. M. Paradise, M. Ouellet, K. J. Fisher, K. L. Newman, J. M. Mdungu, K. A. Ho, R. A. Eachus, T. S. Ham, J. Kirby, M. C. Y. Chang, S. T. Withers, Y. Shiba, R. Sarpong and J. D. Keasling (2006). "Production of the antimalarial drug precursor artemisinic acid in engineered yeast." Nature 440: 940-943.

Shimoni, Y., G. Friedlander, G. Hetzroni, G. Niv, S. Altuvia, O. Biham and H. Margalit (2007). "Regulation of gene expression by small non-coding RNAs: a quantitative view." Mol. Syst. Biol. 3: 138.

Singh, J. and K. P. Gupta (2003). "Calcium glucarate prevents tumor formation in mouse skin." Biomed. Environ. Sci. 16(1): 9-16.

Singh, J. and K. P. Gupta (2007). "Induction of apoptosis by calcium D-glucarate in 7,12-dimethyl benz[a]anthracene-exposed mouse skin" J. Environ. Pathol. Toxicol. Oncol. 26(1): 63-73.

Snoep, J. L., N. Arfman, L. P. Yomano, R. K. Fliege, T. Conway and L. O. Ingram (1994). "Reconstitution of glucose uptake and phosphorylation in a glucose-negative mutant of Escherichia coli by using Zymomonas mobilis genes encoding the glucose facilitator protein and glucokinase." J. Bacteriol. 176(7): 2133-2135.

Srivastava, R., H. J. Cha, M. S. Peterson and W. E. Bentley (2000). "Antisense downregulation of $\sigma^{32}$ as a transient metabolic controller in Escherichia coli: effects on yield of active organophosphorous hydrolase." Appl. Environ. Microbiol. 66(10): 4366-4371.

Tummala, S. B., S. G. Junne and E. T. Papoutsakis (2003). "Antisense RNA downregulation of coenzyme A transferase combined with alcohol-aldehyde dehydrogenase overexpression leads to predominantly alcoholgenic Clostridium acetobutylicum fermentations." J. Bacteriol. 185(12): 3644-3653.

Tummala, S. B., N. E. Welker and E. T. Papoutsakis (2003). "Design of antisense RNA constructs for downregulation of the acetone formation pathway of Clostridium acetobutylicum." J. Bacteriol. 185(6): 1923-1934.

Van den Berg, W. A. M., W. M. A. M. Van Dongen and C. Veeger (1991). "Reduction of the amount of periplasmic hydrogenase in Desulfovibrio vulgaris (Hildenborough) with antisense RNA: direct evidence for an important role of this hydrogenase in lactate metabolism." J. Bacteriol. 173(12): 3688-3694.

Wagner, E. G. H. and R. W. Simons (1994). "Antisense RNA control in bacteria, phages, and plasmids." Annu. Rev. Microbiol. 48: 713-742.

Walaszek, Z., J. Szemraj, M. Hanausek, A. K. Adams and U. Sherman (1996). "D-glucaric acid content of various fruits and vegetables and cholesterol-lowering effects of dietary D-glucarate in the rat." Nutr. Res. 16(4): 673-681.

Wang, B. and H. K. Kuramitsu (2005). "Inducible antisense RNA expression in the characterization of gene functions in Streptococcus mutans." Infect. Immun. 73(6): 3568-3576.

Weisser, P., R. Kramer, H. Sahm and G. A. Sprenger (1995). "Functional expression of the glucose transporter of Zymomonas mobilis leads to restoration of glucose and fructose uptake in Escherichia coli mutants and provides evidence for its facilitator action." J. Bacteriol. 177(11): 3351-3354.

Werpy, T. and G. Petersen (2004). Top value added chemicals from biomass. Volume I: Results of screening for potential candidates from sugars and synthesis gas. N. R. E. L. (NREL) and P. N. N. L. (PNNL).

Wilson, T., G. W. de Lisle, J. A. Marcinkeviciene, J. S. Blanchard and D. M. Collins (1998). "Antisense RNA to ahpC, an oxidative stress defence gene involved in isoniazid resistance, indicates that AhpC of Mycobacterium bovis has virulence properties." Microbiol. 144: 2687-2695.

Yi, J., K. M. Draths, K. Li and J. W. Frost (2003). "Altered glucose transport and shikimate pathway product yields in E. coli." Biotechnol. Prog. 19(5): 1450-1459.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Those skilled in the art will recognize, or be able to ascertain using no more than routine experimentation, many equivalents to the specific embodiments of the invention described herein. Such equivalents are intended to be encompassed by the following claims. All references, including patent documents, disclosed herein are incorporated by reference in their entirety, particularly for the disclosure referenced herein.

What is claimed is:

1. A method for redirecting glycolytic flux in a *E. coli* cell, the method comprising reducing expression of the phosphoenolpyruvate (PEP)-dependent glucose phosphotransferase system (PTS) in the cell and inhibiting phosphorylation of glucose by glucokinase within the cell, wherein the cell has increased expression of galactose permease (ga/P) and/or glucose facilitator protein (glf), wherein inhibiting phosphorylation of glucose by glucokinase within the cell comprises reducing expression of glucokinase in the cell, wherein reducing expression of glucokinase in the cell comprises recombinantly expressing in the cell an antisense RNA transcript that targets glucokinase, or replacing the promoter of glukokinase with a repressible promoter.

2. The method of claim 1, wherein expression of glucose-6-phosphate isomerase in the cell is reduced.

3. The method of claim 2, wherein reduced expression of glucose-6-phosphate isomerase in the cell comprises recombinantly expressing in the cell an antisense RNA transcript that targets glucose-6-phosphate isomerase.

4. The method of claim 1, wherein the cell recombinantly expresses an inducible repressor protein that represses glucokinase expression.

5. The method of claim 1, wherein the cell is a microbial cell.

6. The method of claim 1, wherein the method is a method of producing gluconate and the method further comprises culturing the cell and optionally recovering gluconate from the cell and/or cell culture, or wherein the method is a method of producing glucaric acid and the method further comprises culturing the cell and optionally recovering glucaric acid from the cell and/or cell culture.

7. The method of claim 1, wherein the cell recombinantly expresses a gene encoding for glucose dehydrogenase (gdh).

8. The method of claim 1, wherein the cell recombinantly expresses a gene encoding for galactose permease (galP) and/or glucose facilitator protein (glf).

* * * * *

UNITED STATES PATENT AND TRADEMARK OFFICE
CERTIFICATE OF CORRECTION

PATENT NO. : 8,835,138 B2  
APPLICATION NO. : 13/638026  
DATED : September 16, 2014  
INVENTOR(S) : Kevin Solomon et al.

Page 1 of 1

It is certified that error appears in the above-identified patent and that said Letters Patent is hereby corrected as shown below:

In the Claims:

Column 35, claim 1, line 44, "a *E. coli* cell" should be replaced to read --an *E. coli* cell--

Column 35, claim 1, line 49, "ga/P" should be replaced to read --*galP*--

Column 35, claim 1, line 56, "glukokinase" should be replaced to read --glucokinase--

Signed and Sealed this  
Fourteenth Day of April, 2015

Michelle K. Lee  
*Director of the United States Patent and Trademark Office*